(12) United States Patent
Singh et al.

(10) Patent No.: US 11,767,272 B2
(45) Date of Patent: Sep. 26, 2023

(54) SEARCH METHODS FOR NEW BULK MATERIALS FOR CEMENTING APPLICATIONS

(71) Applicant: Halliburton Energy Services, Inc., Houston, TX (US)

(72) Inventors: John Paul Bir Singh, Kingwood, TX (US); Xueyu Pang, Tomball, TX (US); Aleksey V. Kolasnikov, Houston, TX (US); Stephanie Ruiz, Spring, TX (US); Ronnie Glen Morgan, Waurika, OK (US); Thomas Jason Pisklak, Cypress, TX (US); Krishna Babu Yerubandi, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 347 days.

(21) Appl. No.: 16/633,359

(22) PCT Filed: Apr. 5, 2019

(86) PCT No.: PCT/US2019/026180
§ 371 (c)(1),
(2) Date: Jan. 23, 2020

(87) PCT Pub. No.: WO2020/204960
PCT Pub. Date: Oct. 8, 2020

(65) Prior Publication Data
US 2021/0171406 A1 Jun. 10, 2021

(51) Int. Cl.
*C04B 40/00* (2006.01)
*C04B 28/18* (2006.01)
(Continued)

(52) U.S. Cl.
CPC .......... *C04B 40/0032* (2013.01); *C04B 28/18* (2013.01); *C09K 8/46* (2013.01); *E21B 33/14* (2013.01)

(58) Field of Classification Search
CPC ....... C04B 40/0032; C04B 28/18; C04B 8/46; E21B 33/14
See application file for complete search history.

(56) References Cited

U.S. PATENT DOCUMENTS 4,370,166 A    1/1983  Powers et al.
8,609,595 B2  12/2013  Morgan et al.
(Continued)

FOREIGN PATENT DOCUMENTS

WO      2018156123        8/2018
WO   WO-2018156115 A1 *  8/2018  ............. B28C 7/024
(Continued)

OTHER PUBLICATIONS

ISRWO International Search Report and Written Opinion for PCT/US2019/026180 dated Jan. 6, 2020.
(Continued)

*Primary Examiner* — Crystal J. Lee
(74) *Attorney, Agent, or Firm* — Thomas Rooney; C. Tumey Law Group PLLC

(57) ABSTRACT

A method of cementing may include: providing a first solid particulate material; measuring at least one physicochemical property of the first solid particulate material; correlating the at least one physicochemical property of the first solid particulate material to at least one physicochemical property of a second solid particulate material and at least one physicochemical of a third solid particulate material; determining if a result of the step of correlating meets an operational parameter; and preparing a cement slurry which meets the operational parameter.

20 Claims, 7 Drawing Sheets

(51) Int. Cl.
  *C09K 8/46*  (2006.01)
  *E21B 33/14*  (2006.01)

(56) References Cited

U.S. PATENT DOCUMENTS

| | | |
|---|---|---|
| 11,078,400 B2 | 8/2021 | Pisklak et al. |
| 11,174,198 B2 | 11/2021 | Morgan et al. |
| 11,225,595 B2 | 1/2022 | Jimenez et al. |
| 2010/0081733 A1 | 4/2010 | Michaux et al. |
| 2010/0212892 A1 | 8/2010 | Santra et al. |
| 2015/0321953 A1 | 11/2015 | Porcherie |
| 2017/0364607 A1 | 12/2017 | Kaushik et al. |
| 2018/0355692 A1* | 12/2018 | Sabins .................. C09K 8/426 |
| 2019/0358853 A1 | 11/2019 | Morgan et al. |
| 2019/0367797 A1 | 12/2019 | Morgan et al. |
| 2020/0332172 A1 | 10/2020 | Pisklak et al. |
| 2020/0332643 A1 | 10/2020 | Pisklak et al. |
| 2020/0333318 A1 | 10/2020 | Benkley et al. |
| 2021/0172280 A1 | 6/2021 | Singh et al. |

FOREIGN PATENT DOCUMENTS

| | | | |
|---|---|---|---|
| WO | WO-2018156123 A1 * | 8/2018 | ............. C04B 18/08 |
| WO | 2020204954 A1 | 10/2020 | |

OTHER PUBLICATIONS

PCT Application No. PCT/US2017/018953 dated Feb. 22, 2017.
PCT Application No. PCT/US2017/018928 dated Feb. 22, 2017.

* cited by examiner

SEARCH METHODS FOR NEW BULK MATERIALS FOR CEMENTING APPLICATIONS

BACKGROUND

In well cementing, such as well construction and remedial cementing, cement slurries are commonly utilized. Cement slurries may be used in a variety of subterranean applications. For example, in subterranean well construction, a pipe string (e.g., casing, liners, expandable tubulars, etc.) may be run into a well bore and cemented in place. The process of cementing the pipe string in place is commonly referred to as "primary cementing." In a typical primary cementing method, a cement slurry may be pumped into an annulus between the walls of the well bore and the exterior surface of the pipe string disposed therein. The cement slurry may set in the annular space, thereby forming an annular sheath of hardened, substantially impermeable cement (i.e., a cement sheath) that may support and position the pipe string in the well bore and may bond the exterior surface of the pipe string to the subterranean formation. Among other things, the cement sheath surrounding the pipe string functions to prevent the migration of fluids in the annulus, as well as protecting the pipe string from corrosion. Cement slurries also may be used in remedial cementing methods, for example, to seal cracks or holes in pipe strings or cement sheaths, to seal highly permeable formation zones or fractures, to place a cement plug, and the like.

A particular challenge in cementing may be the development of cement slurries that meet operational objectives and meet required mechanical properties when cured to a set slurry. Oftentimes, cement slurries may be prepared with a base cementitious material, such as Portland cement, and other reactive and non-reactive additives. The additives may provide mechanical properties such as compressive strength to the final set cement and/or needed chemical species for cementitious reactions. Other additives may be included as fillers which may replace a volume of cementitious material while maintaining the same volume of cement and keeping mechanical properties within specification.

Large volumes of cement additives are regularly moved between locations to provide additives to regions where the additives are needed. There may be significant overhead associated with material handling and transportation of additives between cement plants and/or cementing locations. Sometimes there may be regional sources of additives such as regionally sourced natural glasses, clay, silica, and other additives well known in the art that may be substituted for transported additives. Many of the locally or regionally sourced additives may be comparable to transported additives. Availability alone may not be enough to justify selecting a locally sourced additive over a transported additive for inclusion in a cement slurry as there may be chemical and mineralogical differences between the additives owing to the regional variability of additives. The chemical and mineralogical differences such as water requirement, bulk density, specific gravity, and reactive index lead to selection of one additive over another. As will be described in further detail below, comparison of additive materials may rely on intersections of a specific property that are not readily recognized from simple comparison of additives. Disclosed herein are methods and that allow one of ordinary skill in the art to subjectively predict performance of a cement additive.

BRIEF DESCRIPTION OF THE DRAWINGS

These drawings illustrate certain aspects of some of the embodiments of the present disclosure and should not be used to limit or define the disclosure.

DETAILED DESCRIPTION

The present disclosure may generally relate to cementing methods and systems. Provided herein are methods that may include identifying and categorizing solid particulate materials, such as silica sources, cements, cement additives, and other materials based on physicochemical properties and correlating physicochemical properties to an operational parameter. Some examples of operational parameters may include density, compressive strength, material availability, material logistics, and a material specific property, for example. As discussed above, it may be advantageous to locally source solid particulate materials for inclusion in cements.

Selection of additive solid particulate materials may rely on many factors including but not limited to a specific property and reactivity. In general, an additive that has a relatively favorable specific property and a relatively higher reactivity would be preferable to a solid particulate material that has a relatively unfavorable specific property and a relatively lower reactivity. Specific properties include but not limited to crystalline silica content, specific heat, thermal conductivity, heat content, amount of lime, amorphous silica, alumina, and iron. When evaluating two or more additive solid particulate materials it may be difficult to differentiate between the benefits of including one or the other as will be shown below. Table 2 is an example of an additive list available for a particular region. Table 2 lists the additive species, specific property per pound of additive (Unit/lb.), water requirement (WR) in mass percent of water per unit mass of additive required to fully hydrate the additive, bulk density (BD) in units of mass per volume, specific gravity (SG), and reactivity index (alpha). The Units/lb depend on the specific property being considered. For crystalline silica, amorphous silica, lime, alumina and iron content it is % by wt crystalline silica/lb. Units/lb for other specific property such as specific heat, thermal conductivity, heat content may be similarly defined.

TABLE 1

| Species | Specific property Unit/lb | WR | BD | SG | Alpha |
|---|---|---|---|---|---|
| Class A | 0.4 | 35 | 80.2 | 3.24 | 1 |
| Natural Glass | 0.1885 | 79 | 42.12 | 2.4 | 1.2 |
| Fly Ash | 0.012 | 61 | 31.4 | 2.86 | 1.5 |
| Si Powder | 0.31 | 34 | 18 | 2.31 | 2 |
| Class G | 404 | 34 | 86.82 | 3.3 | 1 |
| Slag | 0.04 | 41 | 63.84 | 2.91 | 1.2 |
| Lightweight Beads | 0.4 | 108 | 27.9 | 0.83 | 2.3 |

In an example, an alternate solid particulate material is desired to be analyzed as an alternative to the present silicon powder of Table 1. Table 2 lists the properties of the alternate solid particulate material that is desired to be studied.

TABLE 2

| | Specific property Unit/lb | WR | BD | SG | Alpha |
|---|---|---|---|---|---|
| Si Powder - Alt | 0.25 | 34 | 18 | 2.3 | 1.25 |

Figure 9:
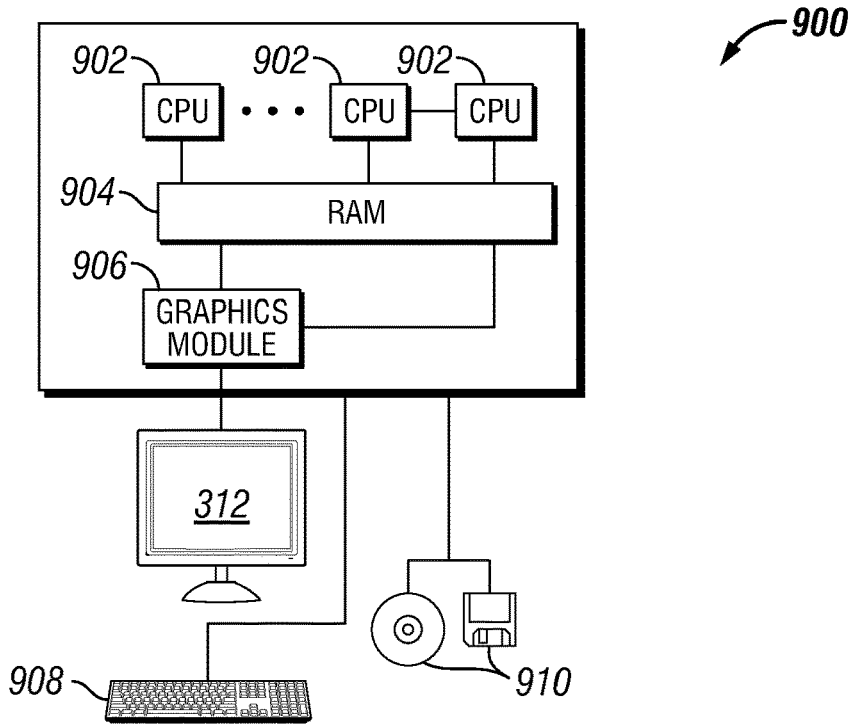
FIG. 9 is a schematic illustration of an example of an information handling system.

The alternative silicon powder appears to have similar properties to the silicon powder of Table 1 with a significantly favorable specific property of 0.25 Units/lb versus 0.31 Units/lb with only a slightly lower reactivity 1.25 versus 2. Some specific properties are highly desirable and need to be maximized while some are undesirable need to be minimized. In this example the need is to lower the value of the specific property and alternate material having a lower value of the specific property is favorable. A method to compare the two solid particulate materials may be to correlate each solid particulate material specific property to reactivity and compare the correlations. In some examples, the correlation may be a regression model calculated by multivariate linear regression. A correlation may be any mathematical model that represents the relationship between the reactivity and the specific property of each solid particulate material. In an example, the correlation may include a linear relationship. FIG. 9 is a plot of the specific property and reactivity (alpha) of the solid particulate material species in Table 1 and Table 2. A linear correlation may be drawn between a base cementitious solid particulate material and the additives that are added to the base cementitious solid particulate material to make a cement blend. In FIG. 9, a line has been drawn between the Portland Class A cement and the Si powder additive solid particulate material. The alternative Si powder from Table 2 is also plotted on FIG. 9. From FIG. 9, it is observed that the alternative Si powder falls below the correlation between the Portland Class A cement and the Si powder. As such, it is indicated that the alternative Si powder has a lower reactivity per unit specific property compared to the Si powder of Table 1 and therefore would not be an effective replacement for the Si powder of Table 1. If alternatively, the alternative Si powder had a specific property of ~0.1 Unit/lb or less or if the reactivity was such that alpha was greater than or equal to 1.75, the alternative Si powder may be considered as a reasonable replacement to the Si powder of Table 1.

A cement slurry, or sometimes referred to herein as a cement slurry, may include cementitious components and water. Cementitious components when not mixed in a cement slurry may be referred to as dry components or dry blend. Cement slurries may also contain non-cementitious components such as additives which are inert and do not contribute to cementitious reactions and additives which may alter properties of the cement slurries, for example.

Water requirement is defined as the minimum quantity of water required to hydrate a quantity of solid particulate material. A cement slurry including solid particulate materials and water therefore has a minimum amount of water per unit mass of the solid particulate materials at which the solid particulate materials and water can be blended together to form the cement slurry. When the minimum amount of water is present, the cement slurry may be referred to as "mixable." Additionally, since dry components in the cement slurry are generally denser than water, a cement slurry that is blended with the minimum quantity of water per unit mass of dry components is usually the highest density at which the cement slurry can be prepared.

A cement slurry may be prepared with water that is in excess of the water requirement up to the point where the cement slurry becomes unstable, also referred to as the upper limit of stability. A cement slurry may become unstable when water is present in an amount that exceeds the maximum sorption capabilities of the dry components of the cement slurry. Unstable cement slurries may be characterized by phase separation of water from the bulk cement slurry. The upper limit of stability may also be the minimum stable density the cement slurry may be mixed to as water is generally less dense than dry components of the cement slurry.

The term mixablility or alternatively, mixable, refers to the ability of the components comprising a cement slurry to blend to form the cement slurry and may be associated with the minimum water requirement of the dry components. The term stability or alternatively, stable, refers to the ability of the components comprising the cement slurry remain in a slurry once blended and may be associated with the upper limit of stability. The American Petroleum Institute (API) publishes industry guideline standards for determining whether a cement slurry is mixable and stable. The API guidelines allow one of ordinary skill in the art to determine if a cement slurry is mixable and stable by performing standardized laboratory tests on the cement slurry.

In some mixability tests, the API recommends specifications and practices for mixing a specific volume of neat cement slurry (i.e. a slurry without dispersing or water extending additives) at certain speeds for certain periods of time to determine if a slurry is mixable. Additives may then be incorporated into the cement slurry and the cement slurry may be re-tested, for example. Some particular cement slurry tests to determine mixability may be found in API RP 10B published on Dec. 1, 1997. One of ordinary skill in the art would be able to perform a mixability test on a cement slurry and determine if the cement slurry is mixable according to API RP 10B. In some stability tests, the API recommends specifications and practices for mixing a specific volume of neat cement slurry (i.e. a slurry without dispersing or water extending additives) at certain speeds for certain periods of time and then placing the neat cement slurry in a container of specified volume. The cement slurry may be observed and a measure of water that phase separates may be measured. Some variants of the stability tests may include performing the tests at elevated temperatures or placing the container at specified angels. Additives may then be incorporated into the cement slurry and the cement slurry may be re-tested, for example. Some particular cement slurry tests to determine stability may be found in API RP 10B published on Dec. 1, 1997. One of ordinary skill in the art would be able to perform a mixability test or a stability test on a cement slurry and determine if the cement slurry is mixable and stable according to API RP 10B.

The term "mixability" or the term "to blend" refers to adequately wetting the surfaces of the dry particles of a cement dry blend when using a standard API RP 10B laboratory procedure for oil well cements. Typical cement slurries have a limited range of water that may be added to form what is referred to as a mixable and stable slurry as discussed above. For example, if too little water is added, the components of the cement slurry may not blend to form a slurry but rather may stay in a relatively separate and non-hydrated state or the final slurry may be too viscous to pump. If too much water is added, the components of the cement slurry may blend to form a slurry but a free water phase may separate from the bulk slurry. Additionally, increased water content in a cement slurry may cause the final set cement to have less compressive strength as compared to a cement slurry prepared with less water.

A cement slurry prepared with too little or too much water may not set to form a hardened mass with satisfactory physical properties. If placed in a subterranean well, such a cement may fail over time resulting in cracks or micro annuli forming between the casing and cement sheath or between the cement sheath and the subterranean formation. The cracks or micro annuli may allow fluid invasion therein which may require remediation. In extreme cases the cement may fail in a manner leading to a loss of well control. In the case of excess water and free water separation, fluid separation may occur at the top of the cement column or in pockets in deviated (e.g. horizontal) wells. In the case of unconventional long horizontal wells, such as but not limited to lengths exceeding 1,000 ft, such cement slurries may become unstable resulting in separation of the cement slurry components resulting a non-homogeneous mixture characterized by free water and an uneven distribution of particulate content. Uneven particulate distribution may result in the particles settling and thus potentially plugging off most or all of the annular cross section, resulting in excessive pumping pressure at the surface. This ultimately results in not being able to complete the cement slurry placement, and hence leaving large portions of the targeted annular space without adequate isolation. These pockets may contribute to annular gas leakage and other annular flow problems. Furthermore, large amounts of free water in a deviated well might lead to a communication channel on the high side in the well bore. These channels may cause gas inflows or undesirable cross flows into the well. If such conditions are allowed to persist, a buildup of annulus pressure may occur resulting in an operating condition which may require intervention. Furthermore, pockets in the cement sheath may present a point of increased casing corrosion which may lead to holes in the casing, casing collapse, loss of well control, and/or abandonment of the well.

A design parameter for a cement slurry may be density. Correct density may be required to ensure that hydrostatic control may be retained throughout a cementing operation. One common method to adjust density of the cement slurry may be to mix the cement slurry with relatively more or relatively less water. Increasing water content in a cement slurry may reduce the density of the cement slurry while reducing the water content of a cement slurry may increase the density. However, as discussed above, water content may determine if the cement slurry is mixable and stable and if the cement slurry will set with the required physical properties.

In general, a solid particulate material may be mixed with an amount of water greater than or equal to the amount specified by the water requirement of the solid particular material to form a slurry. For a solid particulate material i, equation 1 may illustrate the maximum and minimum density achievable for a solid particulate material based on the water requirement of the solid particulate material. The term pi is the density of the solid particulate material, $\rho_w$ is the density of water, $W_i^R$ is the water requirement defined as the minimum weight of water required per unit weigh of solid particulate material i, and a is an amount of water above the minimum required to form a mixable slurry and below the maximum required to form a stable slurry.

$$\rho_{min} \leq \frac{1 + aW_i^R}{\frac{1}{\rho_i} + \frac{aW_i^R}{\rho_w}} \leq \rho_{max} \qquad (1)$$

In an example, an alternate solid particulate material is desired to be analyzed as an alternative to the present lightweight beads of Table 1. Table 3 lists the properties of the alternate solid particulate material that is desired to be studied.

TABLE 3

|  | Specific property Unit/lb | WR | BD | SG | Alpha |
|---|---|---|---|---|---|
| Lightweight Spheres - Alt | 0.25 | 175 | 27.9 | 0.83 | 1 |

The alternative lightweight spheres have similar properties to the lightweight spheres of Table 1 except that the alternative lightweight spheres have a different specific property per unit/lb and have a higher water requirement. In general, a solid particulate material with a higher water requirement may be a favorable solid particulate material to substitute for a solid particulate material with a relatively lower water requirement. However, the specific gravity of the alternative lightweight spheres is lower than that of water which coupled with the higher water requirement of the alternative lightweight spheres means the density of stable and mixable slurries comprising the alternative lightweight spheres will be greater than the density of stable and mixable slurries prepared with the lightweight spheres of Table 1. Table 4 illustrates the some possible densities of slurries prepared with various solid particulate materials.

TABLE 4

|  | Wet mix Density gm/cc |
|---|---|
| Portland Class A | 1.97 |
| Natural Glass | 1.438 |
| Fly Ash | 1.617 |
| Si Powder | 1.687 |
| Portland Class G | 2.002 |
| Slag | 1.803 |
| Lightweight Spheres | 0.915 |
| Lightweight Spheres - Alt | 0.935 |

Figure 1:
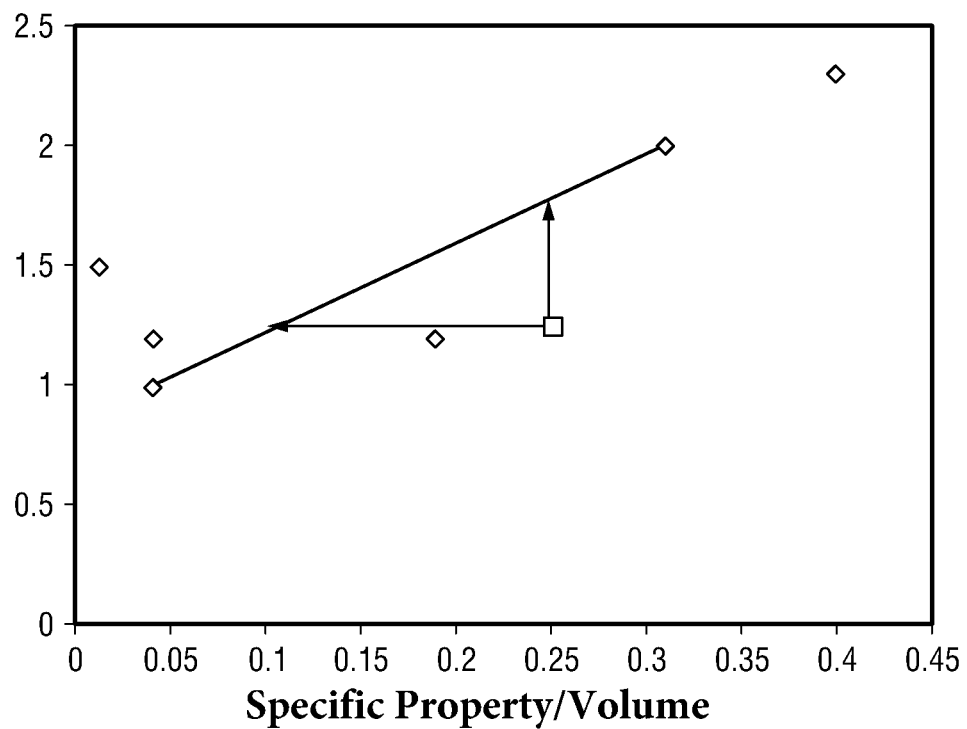
FIG. 1 a plot of a specific property per unit volume of a slurry.
Figure 2:
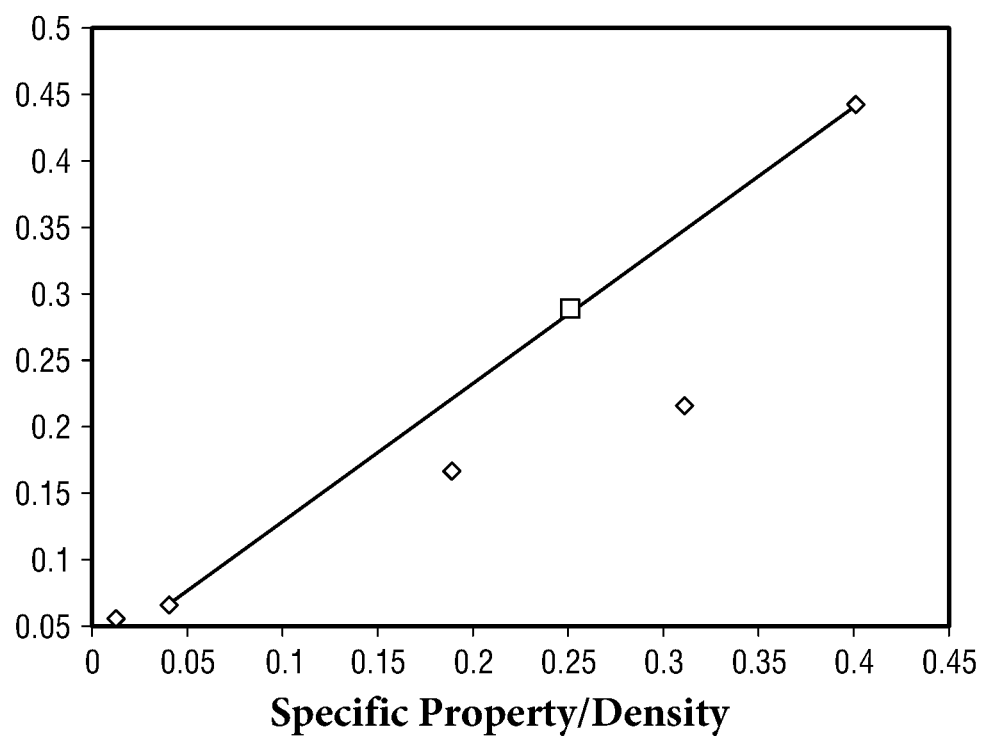
FIG. 2 is a graph of specific property per unit density as a function of specific property for a particular set of materials

The density of a slurry prepared using the lightweight spheres of Table 1 may have a density of about 0.915 gm/cc (grams per cubic centimeter) whereas a slurry prepared using the alternate lightweight spheres may have a density of about 0.935 gm/cc. A method to compare the lightweight spheres and alternate lightweight spheres may be to correlate the specific property per unit volume of the slurry prepared with each solid particulate material as a function of the specific property of the solid particulate material. A correlation may be any mathematical model that represents the relationship between the specific property per unit density of the slurry prepared and the specific property. In an example, the correlation may include a linear relationship. FIG. 1 is a plot of the specific property per unit volume of a slurry prepared with the solid particulate materials of Table 1 as a function of the specific property of the solid particulate material. A linear correlation may be drawn between a base cementitious solid particulate material comprising Portland class A cement and the lightweight spheres of Table 1. The alternative lightweight spheres of Table 3 are also plotted on FIG. 1. From FIG. 1, it is observed that the alternative lightweight spheres are above the correlation between Portland class A cement and the lightweight spheres. More value is obtained from a higher y-axis value on FIG. 1. As such, when a solid particulate material crosses the above the correlation it may be a viable alternative to the solid particulate material used to generate the correlation. A similar methodology may be applied to other solid particulate materials, such as weighting agents, to analyze the specific property per unit volume of the slurry for the weighting agent.

A method of selecting a solid particulate material for use in a cement slurry may include characterizing the solid particulate material by physicochemical methods to determine at least one of specific gravity, free lime content, silica content and phase, alumina content and phase, bulk density, water requirement, and reactivity index. The solid particulate material may be correlated to other solid particulate materials of interest and a comparison between the solid particulate material and other solid particulate materials of interest may be completed to determine which solid particulate materials meet operational parameters. A comparison may include comparing reactivity index per unit specific property of each solid particulate material, for example by generating a plot of specific property versus reactivity. Other correlations and plots may be generated such as, for example, specific property of a component versus slurry specific property per unit volume, specific property versus water requirement, or specific property versus compressive strength. A cement slurry may be prepared which includes the solid particulate material of interest, for example, by comparing where on a plot the solid particulate material of interest is relative to other solid particulate materials, determining if the solid particulate material of interest meets at least one operational parameter based on the position of the solid particulate material of interest is on the plot, and preparing the cement slurry which includes the solid particulate material of interest. For example, if the operational parameter is compressive strength the comparison may be if the solid particulate material of interest meets the compressive strength. Alternatively, or in addition to plotting, the solid particulate material of interest may be compared to other solid particulate materials by other methods such as numerical methods.

The cement slurries may have a density suitable for a particular application. The cement slurries may have any suitable density, including, but not limited to, in the range of about 8 pounds per gallon ("ppg") to about 16 ppg (1 g/cm$^3$ to 1.9 g/cm$^3$) or greater. In the foamed examples, the cement slurries may have a density in the range of about 8 ppg to about 13 ppg (1 g/cm$^3$ to 1.6 g/cm$^3$) or lower.

The water used in the cement slurries may include, for example, freshwater, saltwater (e.g., water containing one or more salts dissolved therein), brine (e.g., saturated saltwater produced from subterranean formations), seawater, or combinations thereof. Generally, the water may be from any source, provided that it does not contain an excess of compounds that may undesirably affect other components in the cement slurry. The water may be included in an amount sufficient to form a pumpable slurry. The water may be included in the cement slurries in any suitable range, including, but not limited to, in the range of about 40% to about 200% by weight of the cement additive ("bwoc"). In some examples, the water may be included in an amount in the range of about 40% to about 150% bwoc.

The cement additive may include two or more cement components. One of the cement components may include a hydraulic cement. A variety of hydraulic cements may be utilized in accordance with the present disclosure, including, but not limited to, those comprising calcium, aluminum, silicon, oxygen, iron, and/or sulfur, which set and harden by reaction with water. Suitable hydraulic cements may include Portland cements, gypsum, and high alumina content cements, among others. Portland cements that are suited for use in the present disclosure may be classified as Classes A, C, G, and H cements according to American Petroleum Institute, API Specification for Materials and Testing for Well Cements, API Specification 10, Fifth Ed., Jul. 1, 1990. In addition, in some examples, cements suitable for use may be classified as ASTM Type I, II, or III. Cement slurries that may be considered "low Portland" may be designed by use of the techniques disclosed herein.

Where present, the hydraulic cement generally may be included in the cement slurries in an amount sufficient to provide the desired compressive strength, density, and simplicity in the design of the cement slurry. The hydraulic cement may be present in the cement slurries in any suitable amount, including, but not limited to, in the range of about 0% to about 99% bwoc. In some examples the hydraulic cement may be present in an amount ranging between any of and/or including any of about 1%, about 5%, about 10%, about 20%, about 40%, about 60%, about 80%, or about 90% bwoc. Cement slurries that are considered "low Portland" may be used, in that the Portland cement (where used) may be present in the cement slurry in an amount of about 40% or less bwoc and, alternatively, about 10% or less. In addition, the cement slurries may also be designed that are free (or essentially free) of Portland cement. Those of ordinary skill in the art, with the benefit of this disclosure, would be able to select an appropriate amount of hydraulic cement for a particular application.

In addition to Portland cement, additional cement components may be used that can be considered alkali soluble. A cement component is considered alkali soluble where it is at least partially soluble in an aqueous solution of pH 7.0 or greater. Certain of the alkali soluble cement components may include a geopolymer cement, which may include an aluminosilicate source, a metal silicate source, and an activator. The geopolymer cement may react to form a geopolymer. A geopolymer is an inorganic polymer that forms long-range, covalently bonded, non-crystalline networks. Geopolymers may be formed by chemical dissolution and subsequent re-condensation of various aluminosilicates and silicates to form a 3D-network or three-dimensional mineral polymer.

The activator for the geopolymer cement may include, but is not limited to, metal hydroxides chloride salts such as KCl, CaCl$_2$, NaCl, carbonates such as Na$_2$CO$_3$, silicates such as sodium silicate, aluminates such as sodium aluminate, and ammonium hydroxide.

The aluminosilicate source for the geopolymer cement may include any suitable aluminosilicate. Aluminosilicate is a mineral comprising aluminum, silicon, and oxygen, plus counter-cations. There are potentially hundreds of suitable minerals that may be an aluminosilicate source in that they may include aluminosilicate minerals. Each aluminosilicate source may potentially be used in a particular case if the specific properties, such as slurry, may be known. Some minerals such as andalusite, kyanite, and sillimanite are naturally occurring aluminosilicate sources that have the same slurry, $Al_2SiO_5$, but differ in crystal structure. Each mineral andalusite, kyanite, or sillimanite may react more or less quickly and to different extents at the same temperature and pressure due to the differing crystal structures. Other suitable aluminosilicate sources may include, but are not limited to, calcined clays, partially calcined clays, kaolinite clays, lateritic clays, illite clays, natural glass, mine tailings, blast furnace slag, and coal fly ash.

The metal silicate source may include any suitable metal silicate. A silicate is a compound containing an anionic silicon compound. Some examples of a silicate include the orthosilicate anion also known as silicon tetroxide anion, $SiO_4^{4-}$ as well as hexafluorosilicate $[SiF_6]^{2-}$. Other common silicates include cyclic and single chain silicates which may have the general formula $[SiO_{2+n}]^{2n-}$ and sheet-forming silicates $([SiO_{2.5}]^-)_n$. Each silicate example may have one or more metal cations associated with each silicate molecule. Some suitable metal silicate sources and may include, without limitation, sodium silicate, magnesium silicate, and potassium silicate.

Where present, the geopolymer cement generally may be included in the cement slurries in an amount sufficient to provide the desired compressive strength, density, and/or simplicity in the design of the cement slurry. The geopolymer cement may be present in the cement slurries in any suitable amount, including, but not limited to, an amount in the range of about 0% to about 99% bwoc. In some examples the geopolymer cement may be present in an amount ranging between any of and/or including any of about 1%, about 5%, about 10%, about 20%, about 40%, about 60%, about 80%, or about 90% bwoc. Those of ordinary skill in the art, with the benefit of this disclosure, would be able to select an appropriate amount of geopolymer cement for a particular application.

Additional cement components that are alkali soluble may be considered a silica source. As used herein, silica has the plain and ordinary meaning of silicon dioxide ($SiO_2$). By inclusion of the silica source, a different path may be used to arrive at a similar product as from Portland cement. For example, a pozzolanic reaction may be induced wherein silicic acid ($H_4SiO_4$) and portlandite ($Ca(OH)_2$ react to form a cement product (calcium silicate hydrate). If other compounds, such as, aluminate, are present in the silica source, additional reactions may occur to form additional cement products, such as calcium aluminate hydrates. Additionally, alumina may be present in the silica source. As used herein, alumina is understood to have the plain and ordinary meaning of aluminum oxide ($Al_2O_3$). Calcium hydroxide necessary for the reaction may be provide from other cement components, such as Portland cement, or may be separately added to the cement slurry. Examples of suitable silica sources may include fly ash, slag, silica fume, crystalline silica, silica flour, cement kiln dust ("CKD"), natural glass, metakaolin, diatomaceous earth, zeolite, shale, and agricultural waste ash (e.g., rice husk ash, sugar cane ash, and bagasse ash), among other. Some specific examples of the silica source will be discussed in more detail below. Where present, the silica source generally may be included in the cement slurry in an amount sufficient to provide the desired compressive strength, density, and simplicity in the design of the cement slurry. The silica source may be present in the cement slurry in any suitable amount, including, but not limited to an amount in the range of about 0% to about 99% bwoc. In some examples the silica source may be present in an amount ranging between any of and/or including any of about 1%, about 5%, about 10%, about 20%, about 40%, about 60%, about 80%, or about 90% bwoc. Those of ordinary skill in the art, with the benefit of this disclosure, would be able to select an appropriate amount of silica source for a particular application.

Amorphous silica may also be present. Amorphous silica may prevent strength retrogression. In general, amorphous silica may not require temperatures above 235° F. to participate in cement hydrations. Amorphous silica may protect against strength retrogression and maximize design efficiency by eliminating the need for multiple designs at different temperatures. Amorphous silica may also replace crystalline silica in some applications.

An example of a suitable silica source may include fly ash. A variety of fly ash may be suitable, including fly ash classified as Class C and Class F fly ash according to American Petroleum Institute, API Specification for Materials and Testing for Well Cements, API Specification 10, Fifth Ed., Jul. 1, 1990. Class C fly ash includes both silica and lime, so it may set to form a hardened mass upon mixing with water. Class F fly ash generally does not contain a sufficient amount of lime to induce a cementitious reaction, therefore, an additional source of calcium ions is necessary for a set-delayed cement slurry comprising Class F fly ash. In some embodiments, lime may be mixed with Class F fly ash in an amount in the range of about 0.1% to about 100% by weight of the fly ash. In some instances, the lime may be hydrated lime.

Another example of a suitable silica source may include slag. Slag is generally a by-product in the production of various metals from their corresponding ores. By way of example, the production of cast iron can produce slag as a granulated, blast furnace by-product with the slag generally comprising the oxidized impurities found in iron ore. Slag generally does not contain sufficient basic solid particulate material, so slag cement may be used that further may include a base to produce a settable slurry that may react with water to set to form a hardened mass. Examples of suitable sources of bases include, but are not limited to, sodium hydroxide, sodium bicarbonate, sodium carbonate, lime, and combinations thereof.

Another example of a suitable silica source may include CKD. Cement kin dust or "CKD", as that term is used herein, refers to a partially calcined kiln feed which is removed from the gas stream and collected, for example, in a dust collector during the manufacture of cement. Usually, large quantities of CKD are collected in the production of cement that are commonly disposed of as waste. CKD is another component that may be included in examples of the cement slurries.

Another example of a suitable silica source may include natural glass. Certain natural glasses may exhibit cementitious properties, in that it may set and harden in the presence of hydrated lime and water. The natural glass may also be ground, for example. Generally, the natural glass may have any particle size distribution as desired for a particular application. In certain embodiments, the natural glass may have a mean particle size in a range of from about 1 micron to about 200 microns. The mean particle size corresponds to d50 values as measured by particle size analyzers such as those manufactured by Malvern Instruments, Worcestershire, United Kingdom. One of ordinary skill in the art, with the benefit of this disclosure, would be able to select a particle size for the natural glass suitable for a chosen application.

Another example of a suitable silica source may include metakaolin. Generally, metakaolin is a white pozzolan that may be prepared by heating kaolin clay, for example, to temperatures in the range of about 600° to about 800° C.

Another example of a suitable silica source may include shale. Among other things, shale included in the cement slurries may react with excess lime to form a suitable cementing solid particulate material, for example, calcium silicate hydrate. A variety of shales are suitable, including those comprising silicon, aluminum, calcium, and/or magnesium. An example of a suitable shale includes vitrified shale. Generally, the shale may have any particle size distribution as desired for a particular application. In certain embodiments, the shale may have a particle size distribution in the range of about 37 micrometers to about 4,750 micrometers.

Another example of a suitable silica source may include zeolite. Zeolites generally are porous alumino-silicate minerals that may be either a natural or synthetic solid particulate material. Synthetic zeolites are based on the same type of structural cell as natural zeolites, and may include aluminosilicate hydrates. As used herein, the term "zeolite" refers to all natural and synthetic forms of zeolite. Examples of zeolites may include, without limitation, mordenite, zsm-5, zeolite x, zeolite y, zeolite a, etc. Furthermore, examples comprising zeolite may include zeolite in combination with a cation such as $Na^+$, $K^+$, $Ca^{2+}$, $Mg^{2+}$, etc. Zeolites comprising cations such as sodium may also provide additional cation sources to the cement slurry as the zeolites dissolve.

The cement slurry may further include hydrated lime. As used herein, the term "hydrated lime" will be understood to mean calcium hydroxide. In some examples, the hydrated lime may be provided as quicklime (calcium oxide) which hydrates when mixed with water to form the hydrated lime. The hydrated lime may be included in examples of the cement slurries, for example, to form a hydraulic slurry with the silica source. For example, the hydrated lime may be included in a silica source-to-hydrated-lime weight ratio of about 10:1 to about 1:1 or a ratio of about 3:1 to about 5:1. Where present, the hydrated lime may be included in the cement slurry in an amount in the range of from about 10% to about 100% by weight of the silica source, for example. In some examples, the hydrated lime may be present in an amount ranging between any of and/or including any of about 10%, about 20%, about 40%, about 60%, about 80%, or about 100% by weight of the silica source. One of ordinary skill in the art, with the benefit of this disclosure, would recognize the appropriate amount of hydrated lime to include for a chosen application.

In some examples, the cement slurry may include a calcium source other than hydrated lime. In general, calcium and a high pH, for example a pH of 7.0 or greater, may be needed for certain cementitious reactions to occur. A potential advantage of hydrated lime may be that calcium ions and hydroxide ions are supplied in the same molecule. In another example, the calcium source may be $Ca(NO_3)_2$ or $CaCl_2$ with the hydroxide being supplied form NaOH or KOH, for example. One of ordinary skill would understand the alternate calcium source and hydroxide source may be included in a cement slurry in the same way as hydrated lime. For example, the calcium source and hydroxide source may be included in a silica source-to-hydrated-lime weight ratio of about 10:1 to about 1:1 or a ratio of about 3:1 to about 5:1. Where present, the alternate calcium source and hydroxide source may be included in the cement slurry in an amount in the range of from about 10% to about 100% by weight of the silica source, for example. In some examples, the alternate calcium source and hydroxide source may be present in an amount ranging between any of and/or including any of about 10%, about 20%, about 40%, about 60%, about 80%, or about 100% by weight of the silica source. One of ordinary skill in the art, with the benefit of this disclosure, would recognize the appropriate amount of alternate calcium source and hydroxide source to include for a chosen application.

A target silica lime ratio may be defined and a cement additive comprising two or more cement components may be identified that meets the silica lime ratio. In some examples, the target silica lime ratio may range from about 80/20 silica to free lime by weight to about 60/40 silica to free lime by weight, for example, be about 80/20 silica to free lime by weight, about 70/30 silica to free lime by weight, or about 60/40 silica to free lime by weight. The silica lime ratio may be determined by measuring the available silica and lime for a given cement component.

Other additives suitable for use in cementing operations also may be included in embodiments of the cement slurry. Examples of such additives include, but are not limited to: weighting agents, retarders, accelerators, activators, gas control additives, lightweight additives, gas-generating additives, mechanical-property-enhancing additives, lost-circulation solid particulate materials, filtration-control additives, fluid-loss-control additives, defoaming agents, foaming agents, dispersants, thixotropic additives, suspending agents, and combinations thereof. One of ordinary skill in the art, with the benefit of this disclosure, would be able to select an appropriate additive for a particular application.

As mentioned previously, in order to determine if two or more of the aforementioned cement components are compatible, several lab tests may be run. Additionally, any potential synergistic effects of the cement component may not be known unless several laboratory tests are performed. Typically, a known cement slurry may be first formulated and tested for properties such as, for example, the 24-hour compressive strength, fluid loss, and thickening time. Then, varying amounts of additives may be added to a fresh batch of cement slurry and the tests are re-run. The results are gathered form each test and compared. A new set of tests may then be run with new concentrations of additives, for example, to adjust properties of the cement slurry. The process of testing various additives in varying concentrations may go on for several trials until an acceptable cement slurry or slurries is formulated. An acceptable cement slurry may be one that meets certain design requirements, such as compressive strength, fluid loss, and thickening time. The cement slurry design process may be done in a heuristic manner leading to a cement slurry that may have the required engineering properties but may not be optimized for the specific property. Additionally, silica sources such as, for example, CKD, have been previously used as either pure fillers or in some examples, reactive components, in Portland based cement slurries. CKD will contribute a portion of silica which requires a portion of lime to react. In methods of cement slurry formulation described above, the heuristic process does not take into account the silica to lime ratio of a slurry.

The method described herein may reduce or eliminate the heuristic search for by a process that identifies a cement additive through a process of measuring and categorizing a variety of cement components referred to as reactivity mapping. Reactivity mapping may generate a correlation between properties of inorganic particles. Reactivity mapping may include several steps. One step may include measuring the physicochemical properties of different solid particulate materials through standardized tests. Another step may include categorizing the solid particulate materials through analysis of data collected and the predicted effect on cement slurry properties. Yet another step may include utilizing the data to estimate solid particulate material reactivity, improve cement performance, predicting blend mechanical properties mathematically based on analytical results, and/or predict slurry density dependence of compressive strength.

Measuring physicochemical properties of each selected cement component may include many laboratory techniques and procedures including, but not limited to, microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological properties, Poisson's Ratio. One or more of the proceeding tests may be consider API tests, as set forth in the API recommended practice for testing well cements (published as ANSI/API recommended practice 10B-2). Additional API tests not specifically listed above may also be used for the measurements. The physicochemical properties may be measured for a group of cement components. Two or more of the cement components measured may be different types of cement components (e.g., natural glass, CKD, fly ash, etc.). Two or more of the cement components may be the same type but from different sources (e.g., natural glass from source 1, natural glass from source 2, etc.).

X-ray powder diffraction is one analysis technique that may be used for measuring the physicochemical properties of the cement components. X-ray powder diffraction is a technique of exposing a sample to x-rays, neutrons, or electrons and measuring the amount of inter-atomic-diffraction. The sample acts a diffraction grating thereby producing a differing signal at different angles. The typical properties that may be measured are the phase identification for the identification and characterization of a crystalline solid. Other properties may be crystallinity, lattice parameters, expansion tensors, bulk modulus, and phase transitions.

X-ray fluorescence is another analysis technique that may be used for measuring the physicochemical properties of the cement components. X-ray fluorescence may use short wave x-rays to ionize atoms in a sample thereby causing them to fluoresce at certain characteristic wavelengths. The characteristic radiation released by a sample may allow accurate identification of the component atoms in the sample as well as their relative amounts.

Particle size analysis is another analysis technique that may be used for measuring the physicochemical properties of the cement components. Particle size analysis may be accomplished through analysis by various laboratory techniques including but not limited to laser diffraction, dynamic light scattering, static image analysis, and dynamic image analysis. Particle size analysis may also provide information about the morphology of a particular sample. Morphology may include parameters such as sphericity and roundness as well as the general shape of a particle such as disk, spheroid, blade, or roller. With a knowledge of the morphology and particle size, the average surface area and volume may be estimated. Surface area and volume may be important in determining the water requirement as well as reactivity. In general, a relatively smaller particle size may react more quickly than a relatively larger particle size. Also the relatively smaller particle size may have a greater water requirement to completely hydrate than a relatively larger particle size.

Energy dispersive x-ray spectroscopy is another analysis technique that may be used for measuring the physicochemical properties of the waste solid particulate materials. Energy dispersive x-ray spectroscopy is an analytical technique used to analyze the elements present in a sample and determine the chemical characterization of a sample. Other techniques may include Fourier transform infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma mass spectrometry (ICP-MS), thermal ionization mass spectroscopy, glow discharge mass spectroscopy, and x-ray photoelectron spectroscopy.

The cement components may be analyzed to determine their water requirement. Water requirement is typically defined as the amount of mixing water that is required to be added to a powdered, solid particulate material to form a slurry of a specified consistency. Water requirement for a particular cement component may be determined by a process that includes a) preparing a Waring blender with a specified amount of water, b) agitating the water at a specified blender rpm, c) adding the powdered solid that is being investigated to the water until a specified consistency is obtained, and d) calculating the water requirement based on the ratio of water to solids required to reach the desired consistency.

The cement components may be analyzed to determine their specific surface area. Specific surface area generally refers to the total surface area and may be reported as the total surface area per unit mass. Values obtained for specific area are dependent on the analysis technique. Any suitable analysis technique may be used, including without limitation adsorption-based methods such as Brunauer-Emmett-Teller (BET) analysis, methylene blue staining, ethylene glycol monoethyl ether adsorption, and a protein-retention method, among other.

Thermogravimetric analysis is another analysis technique that may be used for measuring the physicochemical properties of the cement components. Thermogravimetric analysis is a method of thermal analysis wherein changes in physicochemical properties of a sample may be measured. In general, the properties may be measured as a function of increasing temperature, such as with a constant heating rate, or as a function of time with a constant temperature or a constant mass change. Properties determined by thermogravimetric analysis may include first-order phase transitions and second-order phase transitions such as vaporization, sublimation, adsorption, desorption, absorption, chemisorption, desolvation, dehydration, decomposition, oxidation and reduction reactions, ferromagnetic transition, superconducting transition, and others.

In addition to determining physicochemical properties of the cement components themselves, laboratory tests may also be run to determine behavior of the cement components in a cement slurry. For example, the cement components may be analyzed in a cement slurry to determine their compressive strength development and mechanical properties. For example, a preselected amount of the cement component may be combined with water and lime (if needed for setting). The mechanical properties of the cement slurry may then be determined including, compressive strength, tensile strength, and Young's modulus. Any of a variety of different conditions may be used for the testing so long as the conditions are consistent for the different cement components.

Compressive strength is generally the capacity of a solid particulate material or structure to withstand axially directed pushing forces. The compressive strength of the cement component may be measured at a specified time after the cement component has been mixed with water and the resultant cement slurry is maintained under specified temperature and pressure conditions. For example, compressive strength can be measured at a time in the range of about 24 to about 48 hours (or longer) after the fluid is mixed and the fluid is maintained at a temperature of from 100° F. to about 200° F. and atmospheric pressure. Compressive strength can be measured by either a destructive method or non-destructive method. The destructive method physically tests the strength of treatment fluid samples at various points in time by crushing the samples in a compression-testing machine. The compressive strength is calculated from the failure load divided by the cross-sectional area resisting the load and is reported in units of pound-force per square inch (psi). Non-destructive methods typically may employ an Ultrasonic Cement Analyzer ("UCA"), available from Fann® Instrument Company, Houston, Tex. Compressive strengths may be determined in accordance with API RP 10B-2, *Recommended Practice for Testing Well Cements*, First Edition, July 2005.

Tensile strength is generally the capacity of a solid particulate material to withstand loads tending to elongate, as opposed to compressive strength. The tensile strength of the cement component may be measured at a specified time after the cement component has been mixed with water and the resultant cement slurry is maintained under specified temperature and pressure conditions. For example, tensile strength can be measured at a time in the range of about 24 to about 48 hours (or longer) after the fluid is mixed and the fluid is maintained at a temperature of from 100° F. to about 200° F. and atmospheric pressure. Tensile strength may be measured using any suitable method, including without limitation in accordance with the procedure described in ASTM 0307. That is, specimens may be prepared in briquette molds having the appearance of dog biscuits with a one square inch cross-sectional area at the middle. Tension may then be applied at the enlarged ends of the specimens until the specimens break at the center area. The tension in pounds per square inch at which the specimen breaks is the tensile strength of the solid particulate material tested.

Young's modulus also referred to as the modulus of elasticity is a measure of the relationship of an applied stress to the resultant strain. In general, a highly deformable (plastic) solid particulate material will exhibit a lower modulus when the confined stress is increased. Thus, the Young's modulus is an elastic constant that demonstrates the ability of the tested solid particulate material to withstand applied loads. A number of different laboratory techniques may be used to measure the Young's modulus of a treatment fluid comprising a cementitious component after the treatment fluid has been allowed to set for a period of time at specified temperature and pressure conditions.

Although only some select laboratory techniques may have been mentioned, it should be understood that there may many analytical techniques that may be appropriate or not appropriate for a certain sample. One of ordinary skill in the art with the benefit of this disclosure would be able to select an appropriate analytical technique to determine a certain property of interest.

Once the analytical techniques have been performed on the cement components, the data may be categorized and correlated. Some categories may include, but are not limited to, specific surface area, morphology, specific gravity, water requirement, etc. In some examples, the components may be categorized by relative amounts, including amount of at least one following: silica, alumina, iron, iron, calcium, calcium, sodium, potassium, magnesium, sulfur, oxides thereof, and combinations thereof. For example, the components may be categorized based on an oxide analysis that includes without limitation, silica content, calcium oxide content, and alumina content among other oxides that may be present in the cement component. In addition, correlations between the cement components may be generated based on the data or categorization of the data. Additionally, correlations may be defined or generated between properties of the cement components based on the data. For example, the various categories of properties may be plotted against one another. In some examples, water requirement versus specific surface area may be plotted. Accordingly, the water requirement of the cement component may be correlated to the specific surface area so that the specific surface area is a function of water requirement. Specific surface area may be used to predict reactivity of a cement component (or components). However, specific surface area may not always be available for each solid particulate material as specific surface area analysis typically requires a specialized instrument. Accordingly, if the water requirement may be obtained for the cement component, the correlation between water requirement and specific surface area may be used to obtain an estimate for specific surface area, which may then be used to predict reactivity. In addition to correlations between specific surface area and reactivity, correlations may also be made between specific surface area and other mechanical properties such as tensile strength and Young's modulus.

Some cement components that are alkali soluble may include reclaimed or natural solid particulate materials. Specifically, silica-containing cement components may include solid particulate materials such as mined solid particulate materials, for example natural glass, reclaimed materials, such as fly ash and CKD, and agricultural ashes as previously described. In some examples the cement component that is alkali soluble may have synergistic effects with a Portland cement while others may be incompatible. In some examples a cement component that is alkali soluble may cause gelation, high heat generation, water retention, among other effects. These and other effects may be realized during laboratory testing of the cement component in a cement slurry comprising Portland cement. Laboratory equipment may be configured to detect the effects of the cement component on the slurry. In some examples, equipment such a calorimeter may measure and quantify the amount of heat generation per unit mass of the cement component. Viscometers may measure the increase in gelation caused by the cement component. Each of the physical effects caused by the addition of the cement component may be measured at several concentrations and then categorized, e.g., plotted or mapped. Once a component is mapped, the effect of adding the component to a cement slurry may be predicted by referencing the categorization.

As mentioned previously, some cement components that are alkali soluble may induce gelling when included in a cement slurry. Although a higher gelling rate may be undesirable in some examples, in other examples, a higher gelling rate may be advantageous or necessary to meet the engineering design criteria. Usually one of ordinary skill in the art would select a suitable gelling agent or viscosifier for use in the cement slurry. With the benefit of mapping, one of ordinary skill would be able to select a cement component that is alkali soluble that may serve a dual purpose. For example, a cement component may increase the compressive strength of a cement slurry but also increase the gelling during mixing. If the engineering design criteria requires a higher gelling during mixing, it may be advantageous to include the cement component that increases the compressive strength while also increasing gelling. The inclusion of a cement component that exhibits multiple effects may reduce the amount of additional additives, such as gelling agents or viscosifiers, needed, which may render the cement slurry design more complex. Since the component's gelling effect may have been documented in a map, the amount of component to include in a cement slurry may be readily determined.

Another potentially advantageous physical effect that may be mapped is dispersing ability. Some cement components may include relatively spherical particles. The relatively spherical particles may exert a "roller bearing" effect in a cement slurry with water. The effect may cause the other components in the cement slurry to become more mobile thereby dispersing the components in the cement slurry. If particles that are roughly $1/7^{th}$ or smaller than the primary component in a slurry, then the apparent viscosity may decrease. Another potentially advantageous physical property that may be mapped is surface area. Surface area may relate to density wherein a relatively higher surface area particle may lower the density of a cement slurry. Particles which lower the density may be used as a low-density additive. Another potentially advantageous effect that may be mapped is particle size. Components with relatively smaller particle sizes may have the ability to form a filter cake against a formation thereby blocking cement from escaping into a formation. Cement components with a small particle size may be used as a fluid loss control agent. With the benefit of the present disclosure, one of ordinary skill would be able to select a cement component and map its properties. One of ordinary skill would also be able to select a secondary property of interest of the cement component and with the benefit of the map, create a slurry with the desired properties.

Another potential benefit of replacing traditional cement additives with silica-based cement components is a reduction in complexity of the cement slurry design. A silica-based cement component may partially or fully replace an additive as discussed above. The design of the cement slurry may be improved by balancing the required engineering parameters such as compressive strength, mix ability, free water content, and others in order to maximize the amount of silica-based cement components.

Once the data is collected by the chosen laboratory techniques, categorized, and mapped, several operations may be performed on the data in order to yield predictions about a cement slurry that includes mapped cement components. Set properties, for example, may be estimated. A method of estimating the solid particulate material reactivity based on the reactive index will be described below. Solid particulate material reactivity may be based on many parameters such as specific surface area and specific gravity, among others. Another use for the mapped data may be to increase cement slurry performance based on parameters such as particle shape, particle size, and particle reactivity. The data may also be used to predict and capture slurry density dependence of compressive strength and use the insight gathered to design improved cement formulations. The data may also be used to predict a slurry to achieve an improved cement formulation. The criteria for just right may be compressive strength, total number of components in the cement slurry, rheology, mechanical properties, fluid loss control properties, thickening times, and others.

Reactivity mapping may be used to estimate various mechanical properties of a cement component, including compressive strength, tensile strength, and Young's modulus. As previously described, correlations may be made between specific surface area and certain mechanical properties, such as reactivity, tensile strength, and Young's modulus. Using these correlations, the mechanical properties for a cement component or combination of cement components may be predicted.

One technique that may be used to correlate reactivity and specific surface area is the reactive index. The reactive index may be used in any of the methods previously described. Without being limited by theory, the reactive index of a cement component may be referred to as a measure of the cement component's reactivity as adjusted for differences in surface area. It is important to note that the term "cement component" refers to any solid particulate material that is cementitious when mixed with water and/or lime and a suspending agent, when necessary, such that the slurry is stable. A "cementitious reactive index" $CRI_i$ can be defined as, but not limited to, Equation [2] as follows:

$$CRI_i = f_{CRI}(CS_i, \rho_i, SSA_{PSDi}) \quad [2]$$

Where:
$CS_i$=Unconfined UCS (ultimate compressive strength) obtained from samples cured at specific reference temperature, pressure and age.
$\rho_i$=Density of slurry that was prepared and cured for measuring UCS
$SSA_{PSDi}$=Specific surface area obtained by typical particle size analysis methods.

A "physicochemical index" (PCI) of the cementitious component may be defined as, but not limited to Equation [3]:

$$PCI_i = f_{PCI}(SA_i, SG_i, D_{50}, C_{Si}, C_{Ca}, C_{Al}, C_{Na}, C_{Fe}, C_{other\ species}) \quad [3]$$

Where:
$SA_i$=Surface area of the cementitious component i,
$SG_i$=specific gravity of the cementitious component i,
$D_{50}$=mass average or volume average diameter of the particle size distribution of cementitious component i,
$C_{Si}$=Mass concentration of silica oxide of component i,
$C_{Ca}$=Mass concentration of calcium oxide of component i,
$C_{Al}$=Mass concentration of Aluminum oxide of component i,
$C_{Na}$=Mass concentration of sodium oxide of component i,
$C_{Fe}$=Mass concentration of iron oxide of component i, It should be noted that the mass concentrations referenced above and here to for, may be measured, but is not limited to X-ray fluorescence spectroscopy measuring technique and a reference to "component i" is equivalent to "cementitious component i". The functions in Equations [2] and [3] that define $CRI_i$ and $PCI_i$, when properly defined, the following universal relationship may hold for a wide range of cementitious solid particulate materials such as, but not limited to, Portland cements; fly ash; other pozzolanic solid particulate materials; other ashes; etc.

$$CRI_i = f_{CRI-PCI}(PCI_i) \quad [4]$$

In some examples, the form of Equation [4] may be a power law, such as in Equation [5].

$$CRI_i = A\{PCI_i\}^B \quad [5]$$

A and B are coefficients that may be unique the various species and sources of cementitious solid particulate materials selected. Once the generalized function defined in Equation [5] is defined for a given population or group of cementitious components, a linear or nonlinear summation relationship further defined below, may be used in conjunction with Equation [6] to predict the UCS of various combinations of cementitious solid particulate materials for specified slurry densities, temperatures, pressures and curing age.

$$CRI_c = A\{PCI_c\}^B \quad [6]$$

Where,
$CRI_c$ is defined as the CRI for the unique combination of n cementitious components as the composite, and similarly
$PCI_c$ is defined as the Physicochemical Index for the composite.
A given composite with mass of $m_c$ is defined as:

$$m_c = f_i + f_{i+1} + f_{i+2} + f_n \quad [7]$$

Where: $f_i$ is defined as the mass fraction of the cementitious component i, and n is the total number of independent cementitious components. Once the function is defined in Equation [6], then the composite value of the physicochemical reactive index may be computed using Equation [8] as follows:

$$PCI_c = f_1 PCI_1 + f_2 PCI_2 + f_3 PCI_3 + \ldots + f_n PCI_n \quad [8]$$

Where: $PCI_c$ is defined as the overall chemical reactive index for a blend of n number of uniquely independent cementitious components, $f_i$ is defined as the mass fraction of the cementitious component i, and n is the total number of independent cementitious components. Once $PCI_c$ has been determined for specific assumed blend of selected cementitious components, then the linear or non-linear summations (Equations [9] and [10]) are determined for the following terms:

$$\rho_c = f_1 \rho_1 + f_2 \rho_2 + f_3 \rho_3 + \ldots + f_n \rho_n \quad [9]$$

and $$SSA_{PSDc} = f_1 SSA_{PSD1} + f_2 SSA_{PSD2} + f_3 SSA_{PSD3} + \ldots + f_n SSA_{PSDn} \quad [10]$$

$PCI_c$ is used to compute the value of $CRI_c$ using either Equation [6] or the more generalized form of Equation [4] for the composite terms. Once $CRI_c$ is determined for the given composite blend, then the composite values of $\rho_c$ and $SSA_{PSDc}$ may be used along with Equation [11] to predict the actual compressive strength of the composite blend, $CS_c$.

$$CRI_c = f_{CRI}(CS_c, \rho_c, SSA_{PSDc}) \quad [11]$$

Experimental data was collected for specific composite blends is summarized in the table below:

TABLE 5

Mass Fractions of Cementitious Components

| Cementitious Component | Composite Blend 1 | Composite Blend 2 | Composite Blend 3 |
|---|---|---|---|
| A | 0.36 | | 0.53 |
| B | | 0.32 | |
| C | 0.32 | | 0.31 |
| D | | 0.33 | |
| E | 0.32 | | |
| F | | 0.35 | |
| G | | | 0.16 |
| Totals | 1.00 | 1.00 | 1.00 |

It is important to note that each of the cementitious components above were either distinctly different species (type) of cementitious slurry and/or from a different source.

Additionally, it should be noted that even though a "linear summation" technique is presented in the previous development, that this disclosure also includes other methods such as the non-linear summation method presented in Equation [11].

$$PCI_c = (1+f_1)^{a1} PCI_1 + (1+f_2)^{a2} PCI_2 + (1+f_3)^{a3} PCI_3 + \ldots + (1+f_n)^{an} PCI_n \quad [11]$$

Where: ai are exponents that are determined for a unique set of cementitious components.

Further examples using the chemical reactive index, water requirement and other analytical parameters will now be discussed. A statistical table may be generated that plots chemical reactive index against water requirement. An example is shown in Table 6.

TABLE 6

Chemical Reactive Index Vs. Water Requirement

| Water Requirement | High | X1 | X4, X5 | X8 |
|---|---|---|---|---|
| | Medium | X2 | X6 | X9, X10 |
| | Low | X3 | X7 | X11 ... Xn |
| | | Low | Medium | High |
| | | | Chemical Reactive Index | |

Other analytical parameters such as particle size versus chemical reactive index, heat generation versus chemical reactive index, and others may also be used. By ranking the chemical reactive index against an analytical parameter, a blend of components may be selected that has a favorable specific property and an improved chemical reactive index while still having a mixable slurry. In some examples, a selected cement slurry may have too much free water to set properly. In such examples, a component having a high water requirement may be selected to replace a component in the cement slurry or supplement the cement slurry. The selected component having the high water requirement may be selected based on the chemical reactive index to ensure that the overall blend has sufficient reactivity. A cement slurry comprising the selected cement component may exhibit less free water due to the high water requirement of the component and may also exhibit the same reactivity from selecting the appropriate chemical reactive index. The reactivity of a cement slurry may be tuned based on the selection of cement component having the desired reactivity. A component having a high reactivity may exhibit a faster set time that one with a low reactivity.

The reactivity of a cement slurry may be affected by wellbore temperature. If a wellbore has a relatively low temperature, about <150° F. or less, a component having a relatively higher reactivity may be required to ensure that the cement slurry develops adequate strength. In previous cement slurries, a chemical accelerator may have been used to enhance the reaction speed in a relatively lower temperature well. A cement slurry comprising a relatively higher chemical reactive index component may not require an accelerator due to the high reactivity of the component. Cement slurries comprising a high reactivity component may not require an accelerator and therefore may have a lower total number of components in the cement slurry. If a wellbore has a relatively high temperature, about >150° F. or greater, the cement component may be selected to have a relatively lower reactivity. Selecting a lower reactivity may be advantageous when the high temperature of a wellbore may cause the cement slurry to set too quickly. In previous cement slurries, a cement set retarder may have been used to reduce the reaction speed in a relatively higher temperature well. By selecting a relatively lower reactivity component, the cement set reaction may potentially be slowed without the use of a retarder. Selecting an appropriate cement component based on reactivity may simplify the design of the cement slurry by eliminating or reducing the need for accelerators and retarders. Furthermore, a combination of cement components may be blended to control the reactivity, for example by adding low, medium, and high reactivity cement components, a cement slurry may be created that has a controlled reactivity along the spectrum of wellbore temperatures. One of ordinary skill in the art, with the benefit of this disclosure, would recognize the appropriate amount and type of cement component to include for a chosen application.

Another application of the previously mention statistical correlation may be in classifying cement components by the specific property among other factors. In general, the reactivity of a cement slurry may be maximized to ensure that the cement slurry will attain enough compressive strength to meet the design requirement of a particular well. If a specific cement slurry far exceeds the engineering requirements, then an alternate cement slurry comprising potentially less components may be formulated. The following equations illustrate an improvement scheme for a cement slurry.

$$CRI, \text{composite} = \Sigma(CRI_i * \text{\%Concentration}) \quad [12]$$

$$\text{Cost Index, composite} = \Sigma(\text{Cost}_i * \text{\%Concentration}) \quad [13]$$

$$\text{Optimized Blend} \rightarrow \max CRI, \text{composite} \wedge \min \text{Cost Index, composite} \quad [14]$$

$$\text{Optimization Ratio} = \max\left[\frac{CRi, \text{composite}}{\text{Cost Index, composite}}\right] \quad [15]$$

Constraints: Cost Index<$C, where C≥0

CS=$f$(CRI, analytical properties)→CS, min<CS, composite<CS, max

Using all the techniques previously discussed, a cement slurry having a favorable specific property and a maximized reactivity may be calculated. A first step may be to identify the engineering requirements of a particular well. Another step may be to define the inventory available at a particular field camp or well site. As previously mentioned, a particular region may have access to only a certain amount or kind of cement components. Some of the factors that may be considered in addition to those previously mentioned are the crystalline silica content, specific heat, thermal conductivity, heat content, amount of lime, amorphous silica, alumina, and iron, bulk density, and specific gravity for the available and potential inventory. The available cement components may be tested in a laboratory and classified using the methods previously discussed. Analytical study may include the various analytical techniques previously mentioned along with the physicochemical reactivity measurements for compressive strength, young's modulus, water requirement, and others. Next the correlations between the mechanical performance measures and analytical properties may be calculated. The chemical reactive index may also be calculated. A statistical table of the chemical reactive index and the water requirement may be calculated along with the chemical reactive index versus other selected analytical parameters.

An initial virtual design may be selected and tested to see if it meets the functional requirements defined by the engineering parameters. The initial virtual design may be based on a previous design, chosen from field experience, or selected by a computer. The virtual design may be based on, among other factors, the chemical reactivity of the cement components. The components of the cement slurry may be adjusted iteratively until a cement slurry having the maximum reactive index and favorable specific property is achieved. In some examples, a fluid loss control additive, thickening additive, or other cement additives may be necessary to meet the functional requirements. As was previously described, the amount of cement additives that may need to be added to a cement slurry may be minimized by selecting cement components that have inherent properties such as high reactive index, low water requirement, fluid loss control properties, and dispersive properties, among others.

The cement slurries disclosed herein may be used in a variety of subterranean applications, including primary and remedial cementing. The cement slurries may be introduced into a subterranean formation and allowed to set. As used herein, introducing the cement slurry into a subterranean formation includes introduction into any portion of the subterranean formation, into near wellbore region surrounding the wellbore, or into both. In primary cementing applications, for example, the cement slurries may be introduced into the annular space between a conduit located in a wellbore and the walls of the wellbore (and/or a larger conduit in the wellbore), wherein the wellbore penetrates the subterranean formation. The cement slurry may be allowed to set in the annular space to form an annular sheath of hardened cement. The cement slurry may form a barrier that prevents the migration of fluids in the wellbore. The cement slurry may also, for example, support the conduit in the wellbore. In remedial cementing applications, the cement slurries may be used, for example, in squeeze cementing operations or in the placement of cement plugs. By way of example, the cement slurries may be placed in a wellbore to plug an opening (e.g., a void or crack) in the formation, in a gravel pack, in the conduit, in the cement sheath, and/or between the cement sheath and the conduit (e.g., a microannulus).

While the present description refers to cement slurries and cement components, it should be understood that the techniques disclosed herein may be used with any suitable wellbore treatment slurry and corresponding solid particulates of which cement slurries and cement components are one example. Additional examples of slurry slurries may include spacer fluids, drilling fluids, cleanup pills, lost circulation pills, and fracturing fluids, among others. In addition, while the preceding descriptions describes silica sources, it should be understood that present techniques may be used for mapping other suitable inorganic particulates.

The following statements may describe certain embodiments of the disclosure but should not be read to be limiting to any particular embodiment.

Statement 1. A method of cementing comprising: providing a first solid particulate material; measuring at least one physicochemical property of the first solid particulate material; correlating the at least one physicochemical property of the first solid particulate material to at least one physicochemical property of a second solid particulate material and at least one physicochemical of a third solid particulate material; determining if a result of the step of correlating meets an operational parameter; and preparing a cement slurry which meets the operational parameter.

Statement 2. The method of statement 1 wherein the first solid particulate material includes reactive materials, inert materials, or a combination thereof.

Statement 3. The method of any of statements 2-3 wherein the reactive materials include cementitious materials.

Statement 4. The method of any of statements 2-4 wherein the step of measuring at least one physicochemical property includes measuring water requirement, a reactivity index, a bulk density, a specific gravity, or combinations thereof.

Statement 5. The method of any of statements 2-5 wherein the step of measuring is performed by at least one of microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological property testing, Poisson's Ratio testing.

Statement 6. The method of any of statements 2-6 wherein the step of correlating includes calculating a linear correlation between the at least one physicochemical property of the second solid particulate material and the at least one physicochemical of the third solid particulate material.

Statement 7. The method of any of statements 2-7 wherein the operational parameter includes at least one of density, compressive strength, or specific property selected from crystalline silica content, specific heat, thermal conductivity, heat content, amount of lime, amorphous silica, alumina, iron, and combinations thereof.

Statement 8. A method of selecting a cement component comprising: providing first cement component; correlating at least one physicochemical property and the specific property of the first cement component to at least one physicochemical property and a specific property of a plurality of cement components; determining if the first cement component favorable specific property, the determining based at least partially on the correlation; preparing a cement slurry comprising the first cement component; and pumping the cement slurry.

Statement 9. The method of statement 8 further comprising providing the at least one physicochemical property of the first cement component.

Statement 10. The method of any of statements 8-9 wherein the providing includes providing a water requirement, a reactivity index, a bulk density, a specific gravity, or combinations thereof.

Statement 11. The method of any of statements 8-10 wherein the first cement component includes cementitious materials, weighting agents, retarders, accelerators, activators, gas control additives, lightweight additives, gas-generating additives, mechanical-property-enhancing additives, lost-circulation materials, filtration-control additives, fluid-loss-control additives, defoaming agents, foaming agents, dispersants, thixotropic additives, suspending agents, and combinations thereof.

Statement 12. The method of any of statements 8-11 wherein the step of correlating includes: selecting a second and a third cement component from the plurality of cement components; computing a mathematical relationship between a physicochemical property of the second and third cement component and the specific property of the second and the third cement component; and comparing the at least one physicochemical property and the specific property of the first cement component to the mathematical relationship.

Statement 13. The method of any of statements 8-12 wherein the mathematical relationship is a linear relationship.

Statement 14. The method of any of statements 8-13 wherein the step of determining is based at least partially of the specific property of the first cement component to the mathematical relationship.

Statement 15. The method of any of statements 8-14 further comprising generating a graph of the mathematical relationship.

Statement 16. A non-transitory computer readable medium having data stored therein representing software executable by a computer, the software including instructions comprising: instructions to generate a correlation between a physicochemical property of a first and a second cement component and a specific property of the first and the second cement component; instructions to compare a physicochemical property and a specific property of a third cement component to the correlation; and instructions to generate a cement slurry based at least partially on the comparison.

Statement 17. The non-transitory computer readable medium of statement 16 wherein the correlation is a linear relationship.

Statement 18. The non-transitory computer readable medium of any of statements 16-17 wherein the step of comparing includes comparing at least one of a water requirement, a reactivity index, a bulk density, a specific gravity, or combinations thereof.

Statement 19. The non-transitory computer readable medium of any of statements 16-18 wherein the first and second cement component include reactive materials, inert materials, or a combination thereof.

Statement 20. The non-transitory computer readable medium of any of statements 16-19 of wherein the instructions to generate include instructions to generate the cement based on at least one of density, compressive strength, or specific property.

Example methods of using the cement slurries will now be described in more detail with reference to FIGS. 1-5. Any of the previous examples of the cement slurries may apply in the context of FIGS. 1-5. Referring now to FIG. 1, the preparation of a cement slurry in accordance with examples will now be described. FIG. 1 illustrates a system 300 for the preparation of a cement slurry and subsequent delivery of the cement slurry to a wellbore in accordance with certain examples. As shown, the cement slurry may be mixed in mixing equipment 305, such as a jet mixer, re-circulating mixer, or a batch mixer, for example, and then pumped via pumping equipment 310 to the wellbore. In some examples, the mixing equipment 305 and the pumping equipment 310 may be disposed on one or more cement trucks. If a cement slurry is to be used, a bulk dry cement may be preformulated and prepared at a bulk cement plant, for example. A cement slurry may be mixed by combing the bulk dry cement in mixing equipment 305 or in other mixing equipment. Liquid additives may be blended with the cement slurry in mixing equipment 305. Pumping equipment 310 may pump the cement slurry to the wellbore.

Figure 3:
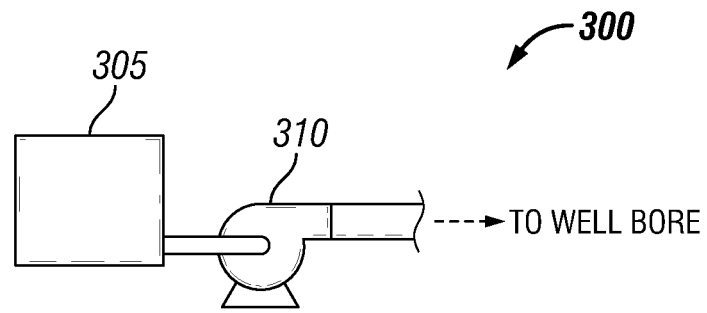
FIG. 3 is a schematic illustration of an example system for the preparation and delivery of a cement slurry into a wellbore.
Figure 4:
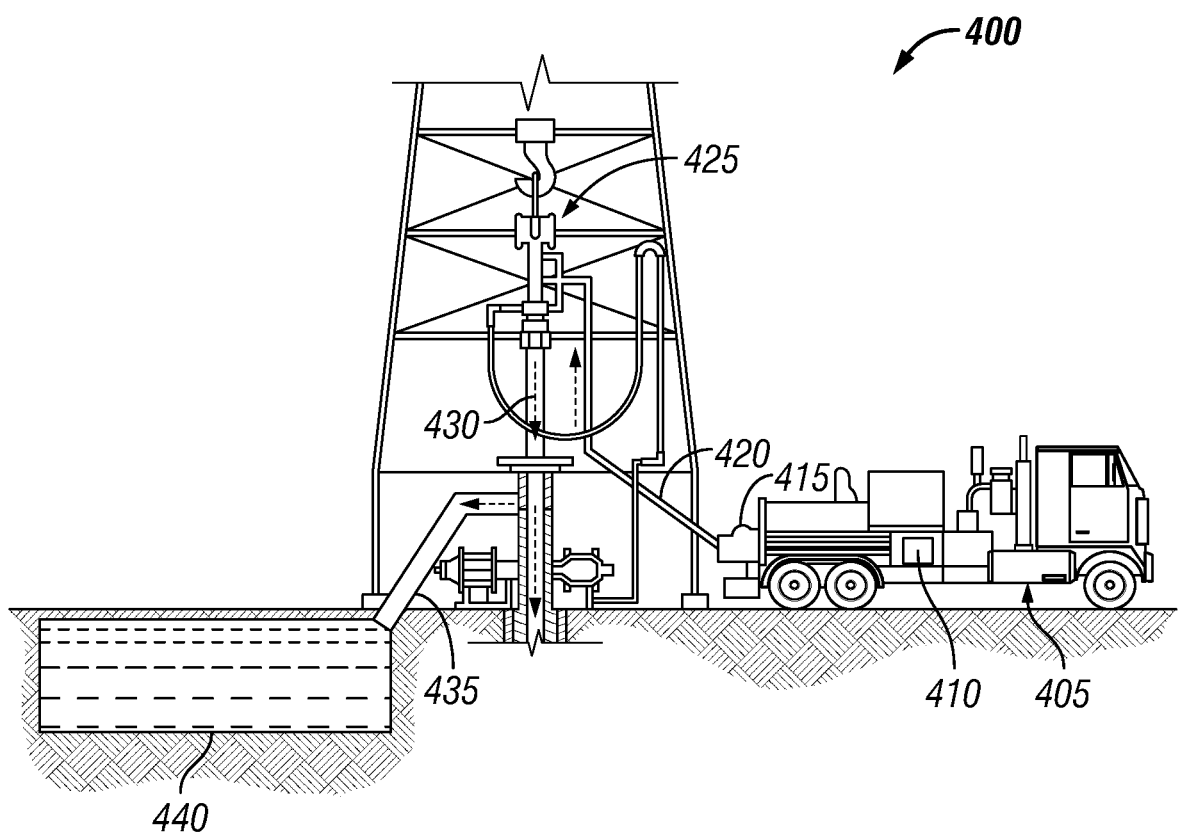
FIG. 4 is a schematic illustration of example surface equipment that may be used in the placement of a cement slurry into a wellbore.

An example primary cementing technique using a cement slurry will now be described with reference to FIGS. 3 and 4. FIG. 3 illustrates surface equipment 400 that may be used in the placement of a cement slurry in accordance with certain examples. It should be noted that while FIG. 3 generally depicts a land-based operation, those skilled in the art will readily recognize that the principles described herein are equally applicable to subsea operations that employ floating or sea-based platforms and rigs, without departing from the scope of the disclosure. As illustrated by FIG. 4, the surface equipment 400 may include a cementing unit 405, which may include one or more cement trucks. The cementing unit 405 may include mixing equipment 410 and pumping equipment 415 (e.g., FIG. 3). Cementing unit 405, or multiple cementing units 405, may pump a cement slurry 430 through a feed pipe 420 and to a cementing head 425 which conveys the cement slurry 430 downhole. Cement slurry 420 may displace other fluids present in the wellbore, such as drilling fluids and spacer fluids, which may exit the wellbore through an annulus and flow through pipe 435 to mud pit 440.

Figure 5:
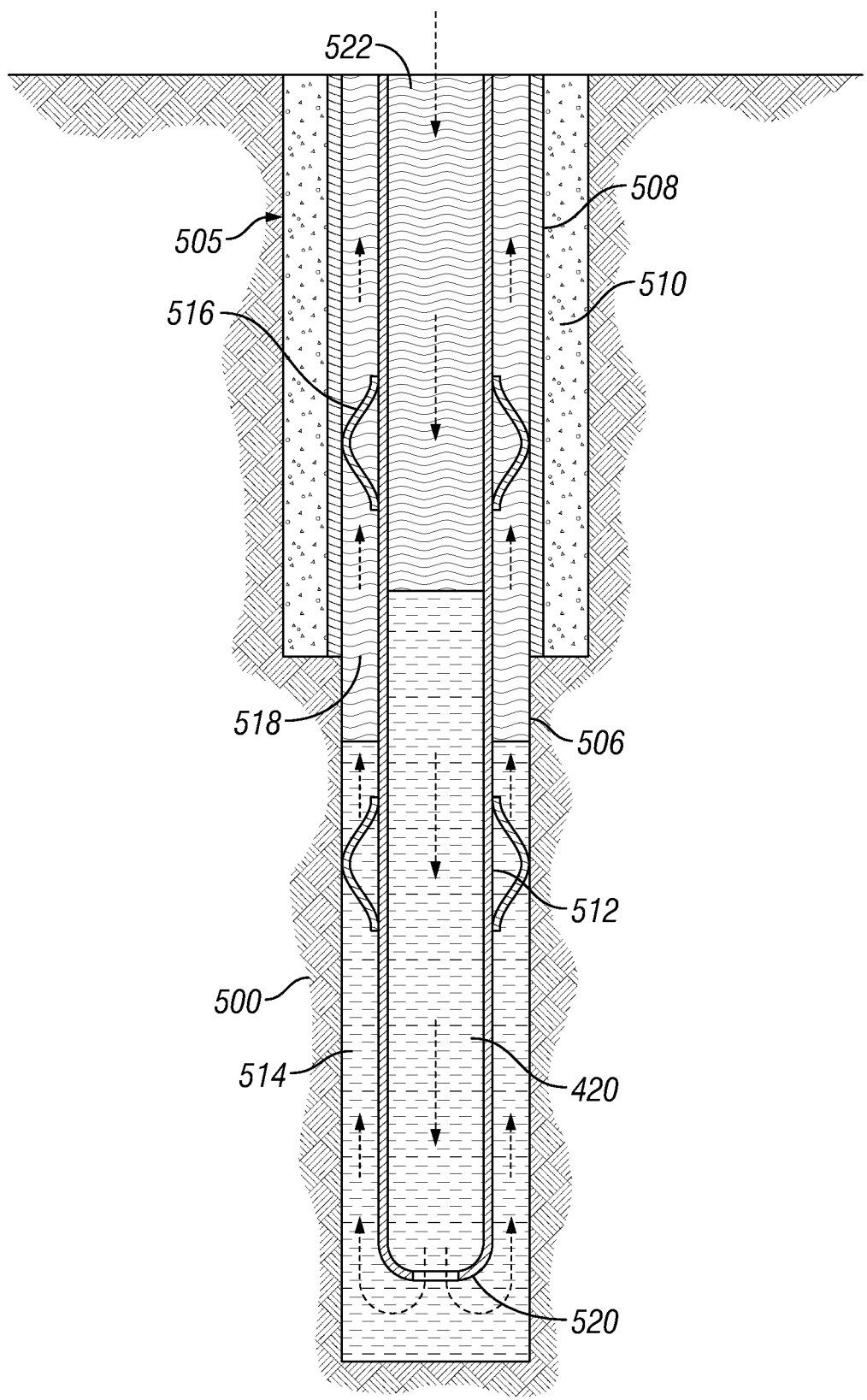
FIG. 5 is a schematic illustration of an example in which a cement slurry is used in a primary cementing application.

FIG. 5 generally depicts the placement of cement slurry 420 into a subterranean formation 500 in accordance with example examples. As illustrated, a wellbore 505 may be drilled into the subterranean formation 500. While wellbore 505 is shown extending generally vertically into the subterranean formation 500, the principles described herein are also applicable to wellbores that extend at an angle through the subterranean formation 500, such as horizontal and slanted wellbores. As illustrated, the wellbore 505 includes walls 506. In the illustrated example, a surface casing 508 has been inserted into the wellbore 505. The surface casing 508 may be cemented in the wellbore 505 by a cement sheath 510. In alternative examples, surface casing 508 may be secured in the wellbore 505 by a hardened resin or hardened resin-cement composite sheath in place of cement sheath 510. In the illustrated example, one or more additional conduits (e.g., intermediate casing, production casing, liners, etc.), shown here as casing 512 may also be disposed in the wellbore 505. As illustrated, there is a wellbore annulus 514 formed between the casing 512 and the walls 506 of the wellbore 505 and/or the surface casing 508. One or more centralizers 516 may be attached to the casing 512, for example, to centralize the casing 512 in the wellbore 505 prior to and during the cementing operation.

With continued reference to FIG. 5, a first spacer fluid 518 may be pumped down the interior of the casing 512. The first spacer fluid 518 may be allowed to flow down the interior of the casing 512 through the casing shoe 520 at the bottom of the casing 512 and up around the casing 512 into the wellbore annulus 514. After the first spacer fluid 518 has been pumped into the casing 512, cement slurry 240 may be pumped into the casing 512. In a manner similar to pumping the first spacer fluid 518, the cement slurry 420 may be allowed to flow down the interior of the casing 512 through the casing shoe 520 at the bottom of the casing 512 and up around the casing 512 into the wellbore annulus 514. After the cement slurry 420 has been pumped into the casing 512, a second spacer fluid 522 may be pumped into casing 512 and allowed to flow down the interior of the casing 512. The first spacer fluid 518 and the second spacer fluid 522 may be used to separate the cement slurry 420 from fluids introduced into the wellbore 505 either in front of or behind the cement slurry 420. Once the cement slurry 420 has been placed into the desired position in the wellbore annulus 514, the cement slurry 420 may be allowed to set in the wellbore annulus 514, for example, to form a hardened resin sheath that supports and positions the casing 512 in the wellbore 505. Alternatively, one or no spacer fluids may be used, and cement slurry 420 may not need to be separated from other fluids introduced previously or subsequently into wellbore 505. While not illustrated, other techniques may also be utilized for introduction of the cement slurry 420. By way of example, reverse circulation techniques may be used that include introducing the cement slurry 420 into the subterranean formation 500 by way of the wellbore annulus 514 instead of through the casing 512. These techniques may also utilize a first spacer fluid 518 and a second spacer fluid 522, or they may utilize one or none spacer fluids. As it is introduced, the cement slurry 420 may displace the first spacer fluid 518. At least a portion of the first spacer fluid 518 may exit the wellbore annulus 514 via a flow line 38 and be deposited, for example, in one or more mud pits 440, as shown on FIG. 4.

Figure 6:
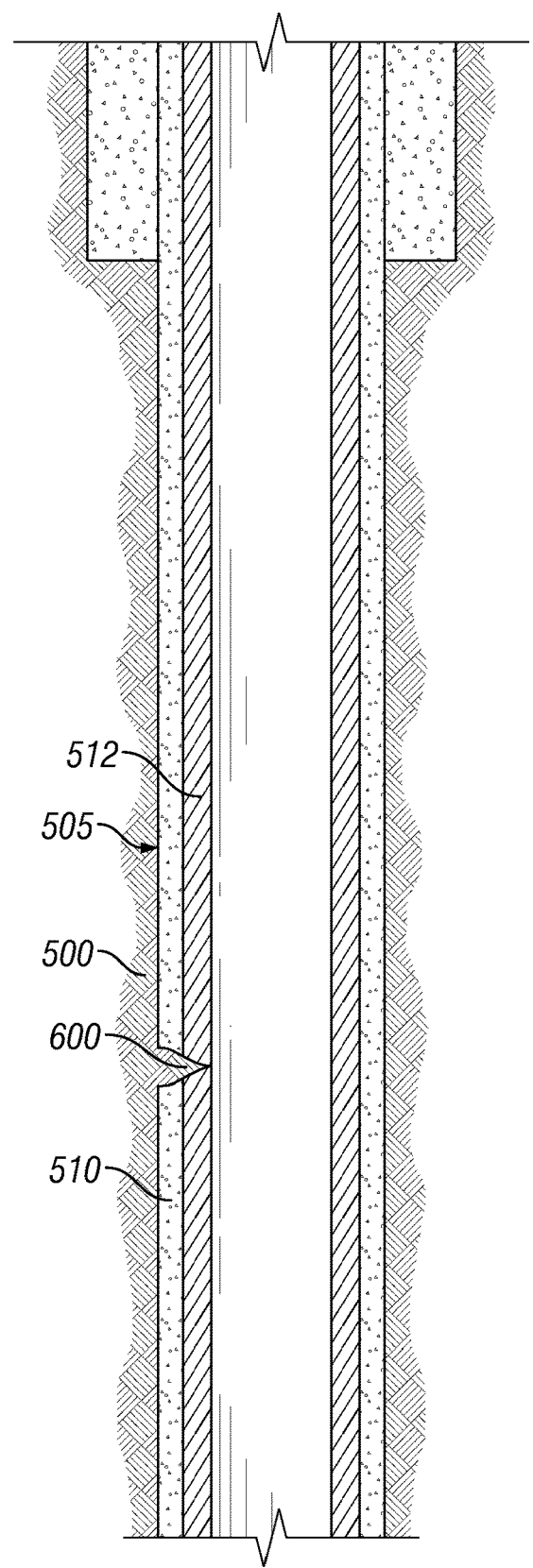
FIG. 6 is a schematic illustration showing the presence of a small perforation in a casing and cement sheath in a wellbore.
Figure 7:
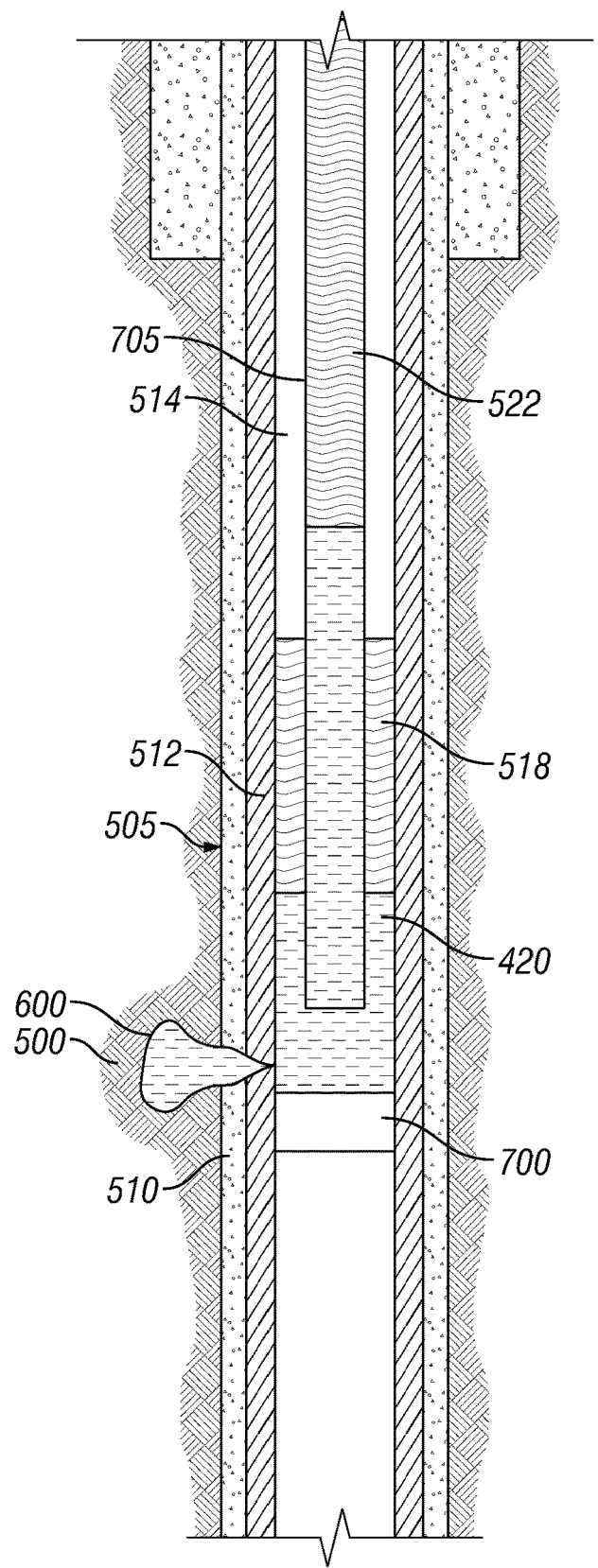
FIG. 7 is a schematic illustration of an example in which a cement slurry is used in a remedial cementing application.
Figure 8:
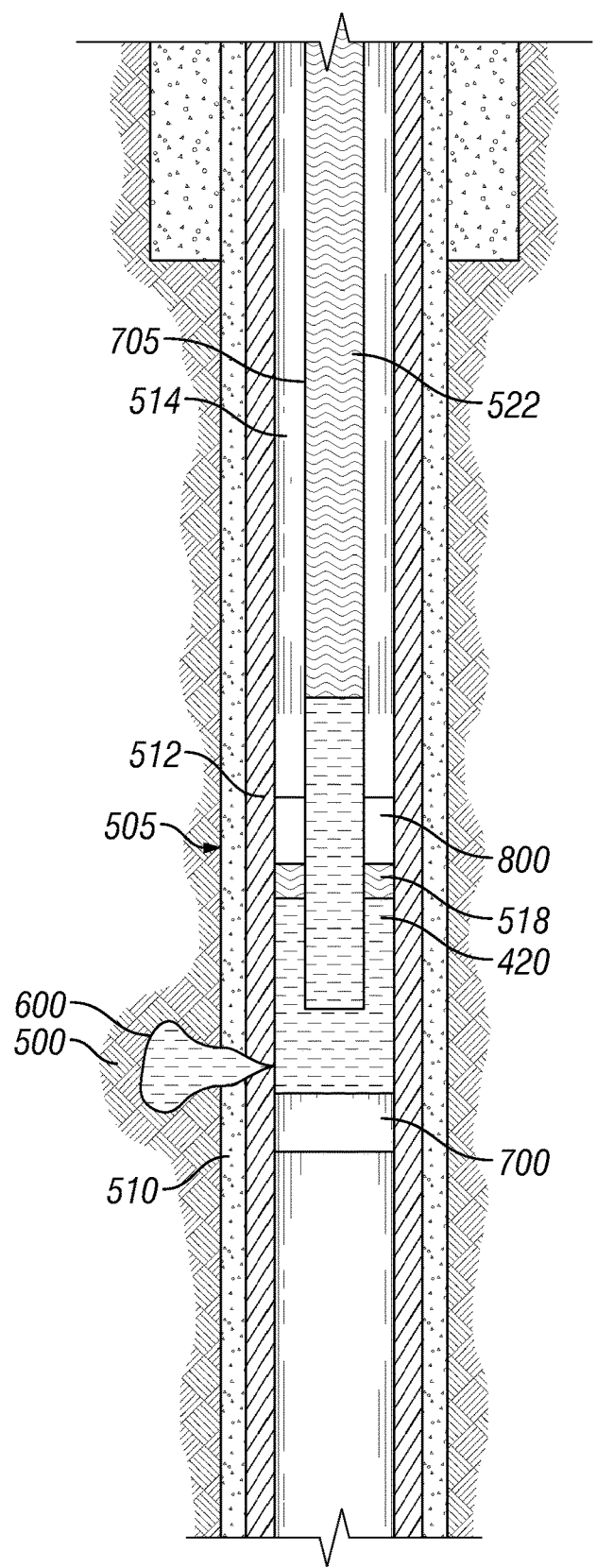
FIG. 8 is a schematic illustration of another example in which a cement slurry is used in a remedial cementing application.

FIGS. 6-8 illustrate methods of remedial or secondary cementing. Turning now to FIG. 6, there is shown a partial cross-section of a conventional producing wellbore 505 that has a primary cemented casing 512. The cement sheath 510 around the casing 512 may have defects potentially caused by a variety of issues, such as improper curing of the cement sheath 510 while it was being formed. Alternatively, the primary cementing may have been successful, but due to adverse temperatures and pressures within the subterranean formation 500, the casing 512 and/or the cement sheath 510 surrounding the casing 512 may form cracks or other types of small perforations 600. The small perforations 600 may be problematic since they may facilitate the introduction of undesirable fluids into the casing 512. As shown in FIG. 4, a small perforation 600 has formed in the cement sheath 510 and the casing 512, potentially allowing the introduction of undesirable fluids into the interior of the casing 512.

Referring now to FIG. 7, a small perforation 600 may be filled or plugged by a cement slurry 420 or a resin-cement composite. A plug 602 (the plug 602 may be any type of plug, e.g., bridge plug, etc.) may be initially placed adjacent and below the small perforation 600, to form a barrier to prevent cement slurry 420 from flowing down the wellbore 505 and therefore allow cement slurry 420 of the present disclosure to fill the small perforations 600 in the casing 512 and cement sheath 510. As shown in FIG. 5, tubing 605 (e.g., coiled tubing, drill pipe, etc.) may be lowered into wellbore 505. A first spacer fluid 518 may be pumped into the wellbore 505 via the tubing 605 and allowed to flow down the interior of the tubing 605 and into the blocked section of the wellbore 505 created by the plug 602. A portion of the first spacer fluid 518 may then flow through the small perforation 600 while another portion may reside in the annulus 514. After pumping the first spacer fluid 518 through the tubing 605, the cement slurry 420 may be pumped through the tubing 605. The cement slurry 420 may be pumped down the interior of the tubing 605 and into the blocked section of the wellbore 505 created by the plug 602. A portion of the cement slurry 420 may then flow through the small perforation 600 while another portion may reside in the annulus 514. The cement slurry 420 may be allowed to set in the small perforation 600 and in a portion of the wellbore annulus 514, for example, to form a hardened mass that seals small perforation 600 to prevent the migration of undesirable fluids into the interior of the casing 512. After the cement slurry 420 has been pumped into the tubing 605, a second spacer fluid 522 may be pumped into the tubing 605 and allowed to flow down the interior of the tubing 605 into the blocked section of the wellbore 505 created by the plug 602 and up around the tubing 605 into the wellbore annulus 514. Alternatively, one or no spacer fluids may be used, and cement slurry 420 may not need to be separated from other fluids introduced previously or subsequently into wellbore 505. The tubing 605 may then be removed. The plug 602 may also be removed. In alternative examples, plug 602 may remain in the wellbore 505 and be drilled through. After tubing 605 is removed, the portion of the hardened cement slurry 420 remaining in the wellbore 505 (i.e., the portion not in the small perforation 600) may then be drilled through.

FIG. 8 describes another example of filling a small perforation 600 with a cement slurry 420. A plug 602 (the plug 602 may be any type of plug, e.g., bridge plug, etc.) may be initially placed adjacent and below the small perforation 600, to form a barrier that may allow pressurized pumping of a cement slurry 420 of the present disclosure to fill any small perforations 600 in the casing 512 and cement sheath 510. As shown in FIG. 6, tubing 605 (e.g., coiled tubing, drill pipe, etc.) may be lowered into wellbore 505. Tubing 605 may be attached to a retainer 604 or may be inserted into a retainer 604 already placed into the wellbore 505. Retainer 604 may allow for the pressurized pumping of the cement slurry 420 into any small perforations 600. Retainer 604 must be placed adjacent to and above the small perforations 600 to be filled by cement slurry 420. Retainer 604 may be any type of retainer, for example, a cement retainer. After plug 602, tubing 605, and retainer 604 are placed, a first spacer fluid 518 may be pumped into the wellbore 505 via the tubing 605 and allowed to flow down the interior of the tubing 605 and into the blocked section of the wellbore 505 created by the plug 602. A portion of the first spacer fluid 518 may then flow through the small perforation 600. After pumping the first spacer fluid 518 through the tubing 605, the cement slurry 420 may be pumped through the tubing 605. The cement slurry 420 may be pumped down the interior of the tubing 605 and into the blocked section of the wellbore 505 created by the plug 602. A portion of the cement slurry 420 may then flow through the small perforation 600 while another portion may reside in the space formed between the plug 602 and retainer 604. The cement slurry 420 may be allowed to set in the small perforation 600 and in the space formed between the plug 602 and retainer 604. The cement slurry 420 may then harden to form a hardened mass that seals small perforation 600 to prevent the migration of undesirable fluids into the interior of the casing 512. After the cement slurry 420 has been pumped into the tubing 605, a second spacer fluid 522 may be pumped into the tubing 605 and allowed to flow down the interior of the tubing 605 into the blocked section of the wellbore 505 created by the plug 602 and into the space formed between the plug 602 and retainer 604. Alternatively, one or no spacer fluids may be used, and cement slurry 420 may not need to be separated from other fluids introduced previously or subsequently into wellbore 505. The tubing 605 may then be removed. The plug 602 may also be removed. In alternative examples, plug 602 may remain in the wellbore 505 and be drilled through. Retainer 604 may also be removed. Conversely, in alternative examples, retainer 604 may be drilled through. After tubing 605 is removed, the portion of the hardened cement slurry 420 remaining in the wellbore 505 (i.e., the portion not in the small perforation 600) may then be drilled through.

FIG. 9 generally illustrates an example of an information handling system 900 that may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, an information handling system 900 may be a personal computer, a network storage device, or any other suitable device and may vary in size, shape, performance, functionality, and price. In examples, information handling system 900 may be referred to as a supercomputer or a graphics supercomputer.

As illustrated, information handling system 900 may include one or more central processing units (CPU) or processors 702. Information handling system 900 may also include a random-access memory (RAM) 904 that may be accessed by processors 902. It should be noted information handling system 900 may further include hardware or software logic, ROM, and/or any other type of nonvolatile memory. Information handling system 900 may include one or more graphics modules 906 that may access RAM 904. Graphics modules 906 may execute the functions carried out by a Graphics Processing Module (not illustrated), using hardware (such as specialized graphics processors) or a combination of hardware and software. A user input device 908 may allow a user to control and input information to information handling system 900. Additional components of the information handling system 900 may include one or more disk drives, output devices 912, such as a video display, and one or more network ports for communication with external devices as well as a user input device 908 (e.g., keyboard, mouse, etc.). Information handling system 900 may also include one or more buses operable to transmit communications between the various hardware components.

Alternatively, systems and methods of the present disclosure may be implemented, at least in part, with non-transitory computer-readable media. Non-transitory computer-readable media may include any instrumentality or aggregation of instrumentalities that may retain data and/or instructions for a period of time. Non-transitory computer-readable media may include, for example, storage media 910 such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

Figure 10:
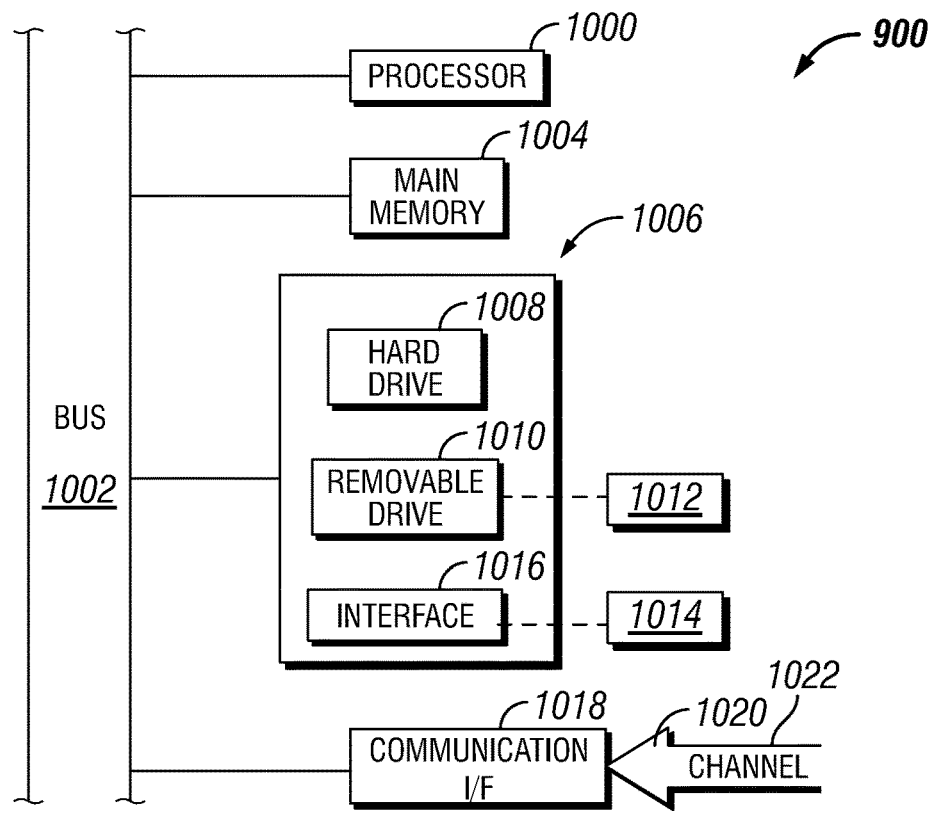
FIG. 10 illustrates additional detail of an information handling system.

FIG. 10 illustrates additional detail of information handling system 900. For example, information handling system 900 may include one or more processors, such as processor 1000. Processor 1000 may be connected to a communication bus 1002. Various software embodiments are described in terms of this exemplary computer system. After reading this description, it will become apparent to a person skilled in the relevant art how to implement the example embodiments using other computer systems and/or computer architectures.

Information handling system 900 may also include a main memory 1004, preferably random-access memory (RAM), and may also include a secondary memory 1006. Secondary memory 1006 may include, for example, a hard disk drive 1008 and/or a removable storage drive 1010, representing a floppy disk drive, a magnetic tape drive, an optical disk drive, etc. Removable storage drive 1010 may read from and/or writes to a removable storage unit 1012 in any suitable manner. Removable storage unit 1012, represents a floppy disk, magnetic tape, optical disk, etc. which is read by and written to by removable storage drive 1010. As will be appreciated, removable storage unit 1012 includes a computer usable storage medium having stored therein computer software and/or data.

In alternative embodiments, secondary memory 1006 may include other operations for allowing computer programs or other instructions to be loaded into information handling system 900. For example, a removable storage unit 1014 and an interface 1016. Examples of such may include a program cartridge and cartridge interface (such as that found in video game devices), a removable memory chip (such as an EPROM, or PROM) and associated socket, and other removable storage units 1014 and interfaces 1016 which may allow software and data to be transferred from removable storage unit 1014 to information handling system 900.

In examples, information handling system 900 may also include a communications interface 1018. Communications interface 1018 may allow software and data to be transferred between information handling system 900 and external devices. Examples of communications interface 1018 may include a modem, a network interface (such as an Ethernet card), a communications port, a PCMCIA slot and card, etc. Software and data transferred via communications interface 1018 are in the form of signals 100 that may be electronic, electromagnetic, optical or other signals capable of being received by communications interface 1018. Signals 1020 may be provided to communications interface via a channel 1022. Channel 1022 carries signals 1020 and may be implemented using wire or cable, fiber optics, a phone line, a cellular phone link, an RF link and/or any other suitable communications channels. For example, information handling system 900 includes at least one memory 1004 operable to store computer-executable instructions, at least one communications interface 1002, 1018 to access the at least one memory 1004; and at least one processor 1000 configured to access the at least one memory 1004 via the at least one communications interface 1002, 1018 and execute computer-executable instructions.

In this document, the terms "computer program medium" and "computer usable medium" are used to generally refer to media such as removable storage unit 1012, a hard disk installed in hard disk drive 1008, and signals 1020. These computer program products may provide software to computer system 900.

Computer programs (also called computer control logic) may be stored in main memory 1004 and/or secondary memory 1006. Computer programs may also be received via communications interface 1018. Such computer programs, when executed, enable information handling system 900 to perform the features of the example embodiments as discussed herein. In particular, the computer programs, when executed, enable processor 1000 to perform the features of the example embodiments. Accordingly, such computer programs represent controllers of information handling system 900.

In examples with software implementation, the software may be stored in a computer program product and loaded into information handling system 900 using removable storage drive 1010, hard disk drive 1008 or communications interface 1018. The control logic (software), when executed by processor 1000, causes processor 1000 to perform the functions of the example embodiments as described herein.

In examples with hardware implementation, hardware components such as application specific integrated circuits (ASICs). Implementation of such a hardware state machine so as to perform the functions described herein will be apparent to persons skilled in the relevant art(s). It should be noted that the disclosure may be implemented at least partially on both hardware and software.

The methods described herein may be carried out, at least in part, using a computer system including a computer-accessible medium, the computer-accessible medium containing a computer program that causes a processor to execute instructions that carry out at least some of the method steps described herein. In general, a computer-accessible medium may include any tangible or non-transitory storage media or memory media such as electronic, magnetic, or optical media—e.g., disk or CD/DVD-ROM coupled to the computer. The terms "tangible" and "non-transitory," as used herein, are intended to describe a computer-readable storage medium (or "memory") excluding propagating electromagnetic signals, but are not intended to otherwise limit the type of physical computer-readable storage device that is encompassed by the phrase computer-readable medium or memory. For instance, the terms "non-transitory computer-readable medium" or "tangible memory" are intended to encompass types of storage devices that do not necessarily store information permanently, including for example, random access memory (RAM), flash memory, or other volatile memory types. Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

The disclosed cement slurries and associated methods may directly or indirectly affect any pumping systems, which representatively includes any conduits, pipelines, trucks, tubulars, and/or pipes which may be coupled to the pump and/or any pumping systems and may be used to fluidically convey the cement slurries downhole, any pumps, compressors, or motors (e.g., topside or downhole) used to drive the cement slurries into motion, any valves or related joints used to regulate the pressure or flow rate of the cement slurries, and any sensors (i.e., pressure, temperature, flow rate, etc.), gauges, and/or combinations thereof, and the like. The cement slurries may also directly or indirectly affect any mixing hoppers and retention pits and their assorted variations.

It should be understood that the slurries and methods are described in terms of "comprising," "containing," or "including" various components or steps, the slurries and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present disclosure is well adapted to attain the ends and advantages mentioned as well as those that are inherent therein. The particular examples disclosed above are illustrative only, as the present disclosure may be modified and practiced in different but equivalent manners apparent to those skilled in the art having the benefit of the teachings herein. Although individual examples are discussed, the disclosure covers all combinations of all those examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method of cementing comprising:
providing a first solid particulate material;
measuring at least one physicochemical property of the first solid particulate material;
correlating the at least one physicochemical property of the first solid particulate material to at least one physicochemical property of a second solid particulate material using a first generated plot;
correlating the at least one physicochemical property of the first solid particulate material to at least one physicochemical of a third solid particulate material using a second generated plot;
determining if the first solid particulate material meets at least one operational parameter by comparing where the first solid particulate material is relative to the second solid particulate material on the first generated plot and where the first solid particulate material is relative to the third solid particulate material on the second generated plot, wherein the at least one operational parameter is selected from the group consisting of density, compressive strength, crystalline silica content, lime content, amorphous silica content, alumina content, iron content, specific heat, thermal conductivity, and combinations thereof;
determining if a cement slurry comprising the first solid particulate is mixable using the equation:

$$\rho_{min} \leq \frac{1 + aW_1^R}{\frac{1}{\rho_1} + \frac{aW_1^R}{\rho_w}} \leq \rho_{max}$$

where $\rho_{min}$ is a minimum density, $\rho_{max}$ is a maximum density, a is an amount of water, $W_i^R$ is a water requirement, $\rho_i$ is a density of the solid particulate material, and $\rho_w$ is a density of water; and
based on the determination, preparing the cement slurry, wherein a cement formed from the cement slurry meets the operational parameter.

2. The method of claim 1, wherein the first solid particulate material comprises reactive materials, inert materials, or a combination thereof.

3. The method of claim 2, wherein the reactive materials comprise cementitious materials.

4. The method of claim 1, wherein the step of measuring at least one physicochemical property comprises measuring water requirement, a reactivity index, a bulk density, a specific gravity, or combinations thereof.

5. The method of claim 1, wherein the step of measuring is performed by at least one of microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological property testing, Poisson's Ratio testing.

6. The method of claim 1, wherein the step of correlating comprises calculating a mathematical relationship between the at least one physicochemical property of the second solid particulate material and the at least one physicochemical of the third solid particulate material.

7. The method of claim 6, wherein the mathematical relationship is a linear correlation.

8. The method of claim 1, wherein the operational parameter further comprises at least one of density or compressive strength.

9. The method of claim 1, wherein the cement slurry comprises Portland cement, the first solid particulate material, and water.

10. The method of claim 1, wherein the cement slurry is introduced into a subterranean formation and allowed to set.

11. The method of claim 1, wherein the first solid particulate material comprises a cement component.

12. The method of claim 1, wherein the cement slurry comprises at least one cement additive selected from the group consisting of cementitious materials, weighting agents, retarders, accelerators, activators, gas control additives, lightweight additives, gas-generating additives, mechanical-property-enhancing additives, lost-circulation materials, filtration-control additives, fluid-loss-control additives, defoaming agents, foaming agents, dispersants, thixotropic additives, suspending agents, and combinations thereof.

13. The method of claim 1, wherein the step of correlating comprises calculating a linear correlation between the at least one physicochemical property of the second solid particulate material and the at least one physicochemical property of the third solid particulate material.

14. The method of claim 1, wherein the at least one operational parameter comprises specific heat requirement or thermal conductivity requirement.

15. The method of claim 14, wherein the at least one operation parameter further comprises $W_i^R$, $\rho_i$, or $\rho_w$.

16. A method of cementing comprising:
provinding a first solid particulate material, wherein the first solid particulate material comprises a cement component, reactive materials, inert materials, or a combination thereof;
measuring at least one physicochemical property of the first solid particulate material;
correlating the at least one physicochemical property of the first solid particulate material to at least one physicochemical property of a second solid particulate material using a first correlation and correlating the first physicochemical property to at least one physicochemical property of a third solid particulate material using a second correlation, wherein the steps of correlating comprise calculating a linear correlation between the at least one physicochemical property of the second solid particulate material and the at least one physicochemical property of the third solid particulate material;
determining if the first solid particulate material meets an operational parameter by comparing the at least one measured physicochemical property of the first solid particulate material with the physicochemical property of the second solid particulate material using the first correlation and the at least one measured physicochemical property of the first solid particulate material with the physicochemical property of the third solid particulate material using the second correlation, wherein a cement slurry comprising the first solid particulate material meets the operational parameter when the first solid particulate material meets the operational parameter;
determining if a cement slurry comprising the first solid particulate is mixable using the equation:

$$\rho_{min} \leq \frac{1 + aW_1^R}{\frac{1}{\rho_1} + \frac{aW_1^R}{\rho_w}} \leq \rho_{max}$$

where $\rho_{min}$ is a minimum density, $\rho_{max}$ is a maximum density, a is an amount of water, $W_i^R$ is a water requirement, $\rho_i$ is a density of the solid particulate material, and $\rho_w$ is a density of water; and
based on the determination, preparing the cement slurry, wherein a cement formed from the cement slurry meets the operational parameter; and
pumping the cement slurry into a subterranean formation.

17. The method of claim 16, wherein the reactive materials comprise cementitious materials.

18. The method of claim 17, wherein the step of measuring at least one physicochemical property comprises measuring a water requirement, a reactivity index, a bulk density, a specific gravity, or combinations thereof.

19. The method of claim 17, wherein the cement component comprises cementitious materials, weighting agents, retarders, accelerators, activators, gas control additives, lightweight additives, gas-generating additives, mechanical-property-enhancing additives, lost-circulation materials, filtration-control additives, fluid-loss-control additives, defoaming agents, foaming agents, dispersants, thixotropic additives, suspending agents, and combinations thereof.

20. The method of claim 17, wherein the cement slurry is allowed to set in the subterranean formation.

* * * * *